US008817253B2

(12) United States Patent
Moshe et al.

(10) Patent No.: US 8,817,253 B2
(45) Date of Patent: *Aug. 26, 2014

(54) HYPER-SPECTRAL IMAGING AND ANALYSIS OF A SAMPLE OF MATTER, FOR IDENTIFYING AND CHARACTERIZING AN OBJECT OF INTEREST THEREIN

(75) Inventors: Danny S. Moshe, Tel-Aviv (IL); Vladimir Weinstein, Rishon-LeZion (IL)

(73) Assignee: Green Vision Systems Ltd., Tel-Aviv (IL)

( * ) Notice: Subject to any disclaimer, the term of this patent is extended or adjusted under 35 U.S.C. 154(b) by 33 days.

This patent is subject to a terminal disclaimer.

(21) Appl. No.: 13/447,430

(22) Filed: Apr. 16, 2012

(65) Prior Publication Data

US 2012/0202192 A1 Aug. 9, 2012

Related U.S. Application Data

(63) Continuation-in-part of application No. 12/527,206, filed as application No. PCT/IL2008/000205 on Feb. 14, 2008, now Pat. No. 8,159,661.

(60) Provisional application No. 60/901,320, filed on Feb. 15, 2007.

(51) Int. Cl.
*G01J 3/00* (2006.01)

(52) U.S. Cl.
USPC .......................... 356/300; 356/307; 435/288.7

(58) Field of Classification Search
USPC ........... 356/300, 307, 326, 328; 435/288.7, 5, 435/29
See application file for complete search history.

(56) References Cited

U.S. PATENT DOCUMENTS 5,876,672 A * 3/1999 Dandliker et al. ......... 422/82.08
6,160,618 A   12/2000 Garner
(Continued)

FOREIGN PATENT DOCUMENTS

| GB | 2459600 | 11/2009 |
|---|---|---|
| WO | WO 03/065009 | 8/2003 |
| WO | WO 2008/099407 | 8/2008 |

OTHER PUBLICATIONS

Patent Modified Examination Report Dated Aug. 31, 2012 From the Australian Government, IP Australia Re. Application No. 2008215781.

(Continued)

*Primary Examiner* — Kara E. Geisel
*Assistant Examiner* — Dominic J. Bologna

(57) ABSTRACT

Method for hyper-spectral imaging and analysis of a sample of matter, for identifying and characterizing an object of interest therein. Preparing test solution or suspension of the sample, including adding thereto a spectral marker specific to object of interest, such that if object of interest is in test solution or suspension, object of interest becomes a hyper-spectrally active target which is hyper-spectrally detectable and identifiable; adding to test solution or suspension a background reducing chemical, for reducing background interfering effects caused by presence of objects of non-interest in test solution or suspension, thereby increasing hyper-spectral detectability of hyper-spectrally active target in test solution or suspension; generating and collecting hyper-spectral image data and information of test solution or suspension; and, processing and analyzing thereof. Exemplary objects of interest are biological agents—bacteria (*Bacillus anthracis*), viruses, fungi, toxins, or, chemical agents—nerve agents (sarin, tabun, soman), and chemical poisons.

20 Claims, 5 Drawing Sheets

> Preparing a test solution or suspension of the

(56) References Cited

U.S. PATENT DOCUMENTS

2003/0138876 A1    7/2003  Ponce et al.
2006/0257891 A1*  11/2006  Farquharson et al. ............ 435/6
2012/0154790 A1*   6/2012  Bodily ............................ 356/51

OTHER PUBLICATIONS

Requisition by the Examiner Dated Mar. 4, 2013 From the Canadian Intellectual Property Office Re. Application No. 2,678,504.
International Preliminary Report on Patentability Dated Aug. 19, 2009 From the International Bureau of WIPO Re.: Application No. PCT/IL2008/000205.
International Search Report Dated Aug. 7, 2008 From the International Searching Authority Re.: Application No. PCT/IL2008/000205.
Notice of Allowance Dated Dec. 12, 2011 From the US Patent and Trademark Office Re. U.S. Appl. No. 12/527,206.
Patents Act 1977: Examination Report Under Section 18(3) Dated Nov. 8, 2010 From the Intellectual Property Office of the United Kingdom Re. Application No. GB0914496.5.
Patents Act 1977: Examination Report Under Section 18(3) Dated Mar. 17, 2011 From the Intellectual Property Office of the United Kingdom Re. Application No. GB 0914496.5.
Patents Act 1977: Patents Rules 2007 Notification of Grant: Patent Serial No. GB2459600 Dated May 14, 2011 From the Intellectual Property Office of the United Kingdom Re. Application No. GB 0914496.5.
Response Dated Mar. 7, 2011 to Patents Act 1977: Examination Report Under Section 18(3) of Nov. 8, 2010 From the Intellectual Property Office of the United Kingdom Re. Application No. GB0914496.5.
Response Dated May 8, 2011 to Patents Act 1977: Examination Report Under Section 18(3) of Mar. 17, 2011 From the Intellectual Property Office of the United Kingdom Re. Application No. GB 0914496.5.
Response Dated May 9, 2011 to Patents Act 1977: Examination Report Under Section 18(3) of Mar. 17, 2011 From the Intellectual Property Office of the United Kingdom Re. Application No. GB 0914496.5.
Written Opinion Dated Aug. 7, 2008 From the International Searching Authority Re.: Application No. PCT/IL2008/000205.
Hindle et al. "Dipicolinic Acid (DPA) Assay Revisited and Appraised for Spore Detection", The Analyst, XP009074432, 124(11): 1599-1604, Nov. 1, 1999. p. 1601-1603.
Lester et al. "An Anthrax 'Smoke' Detector. Online Monitoring of Aerosolized Bacterial Spores", IEEE Engineering in Medicine and Biology, XP0011093233, 21(5): 38-42, Sep. 1, 2002. Abstract, p. 40-41.
Pellegrino et al. "Bacterial Endospore Detection Using Terbium Dipicolinate Photoluminescence in the Presence of Chemical and Biological Materials", Analytical Chemistry, XP002405517, 70(9): 1755-1760, Mar. 24, 1998.
Rosen "Bacterial Endoscope Detection Using Photoluminescence From Terbium Dipicolinate", Reviews in Analytical Chemistry, XP000985266, 18(1/02): 1-21, Apr. 1, 1999. Abstract, p. 13-15.
Office Action Dated Sep. 3, 2012 From the Israel Patent Office Re. Application No. 200397 and Its Translation Into English.

* cited by examiner

> Preparing a test solution or suspension of the sample of matter.

- adding to the sample of matter a spectral marker specific to the object of interest.

- adding to the test solution or suspension a background reducing chemical.

⇩

> Generating and collecting hyper-spectral image data and information of the test solution or suspension.

⇩

> Processing and analyzing the hyper-spectral image data and information.

- identifying and characterizing the hyper-spectrally active target in the test solution or suspension.

- identifying and characterizing the object of interest in the sample of matter.

Fig. 1

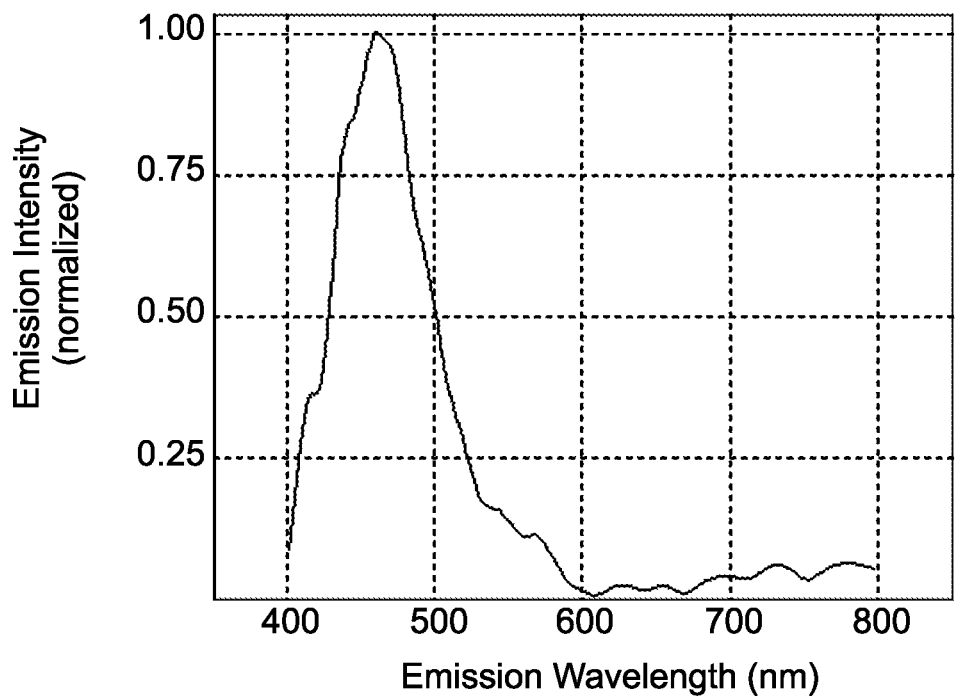
Fig. 2a (dust particle 1)
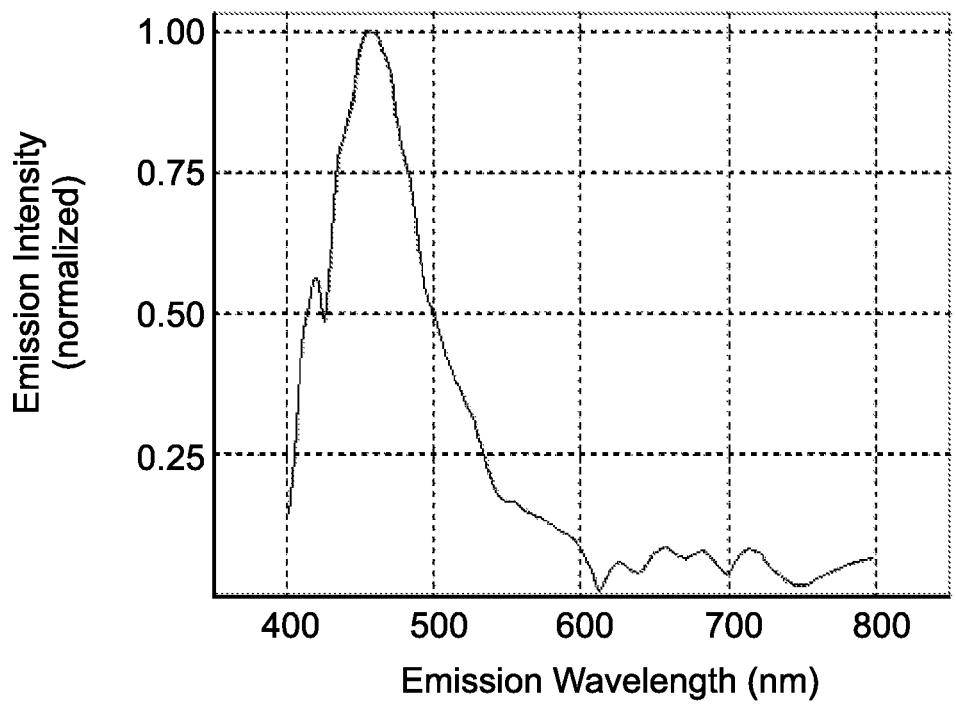
Fig. 2b (dust particle 2)

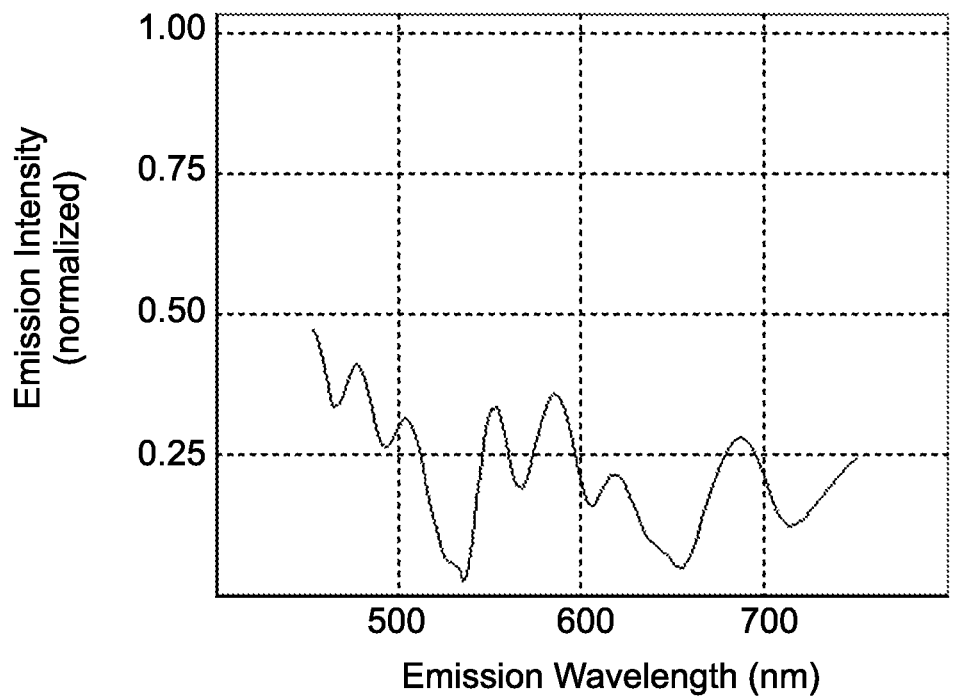
Fig. 3a (background-no spores)
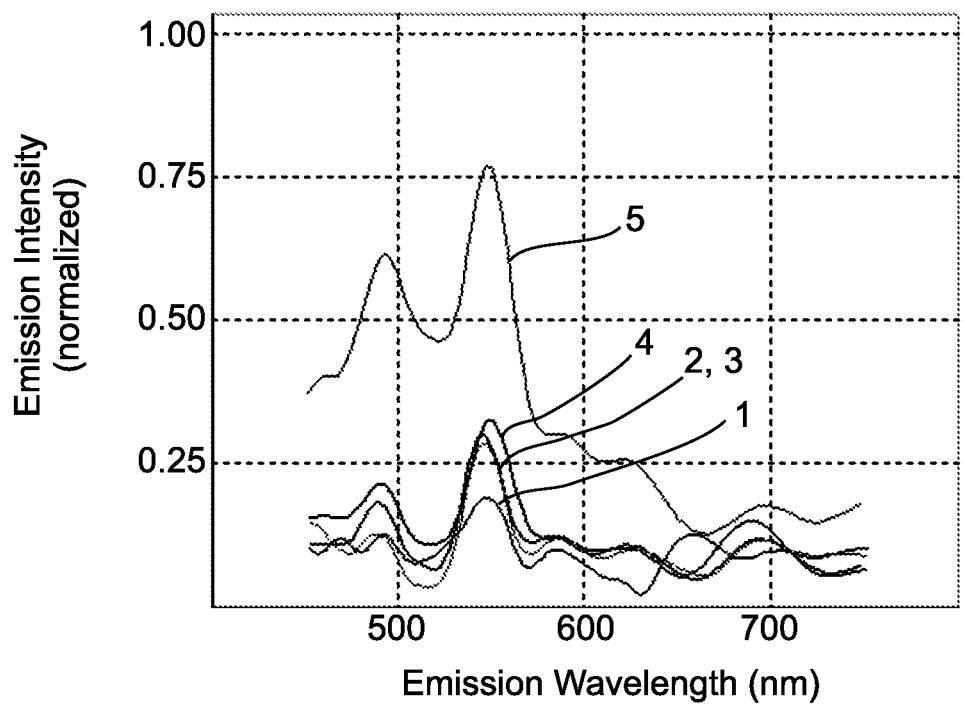
Fig. 3b (with spores)

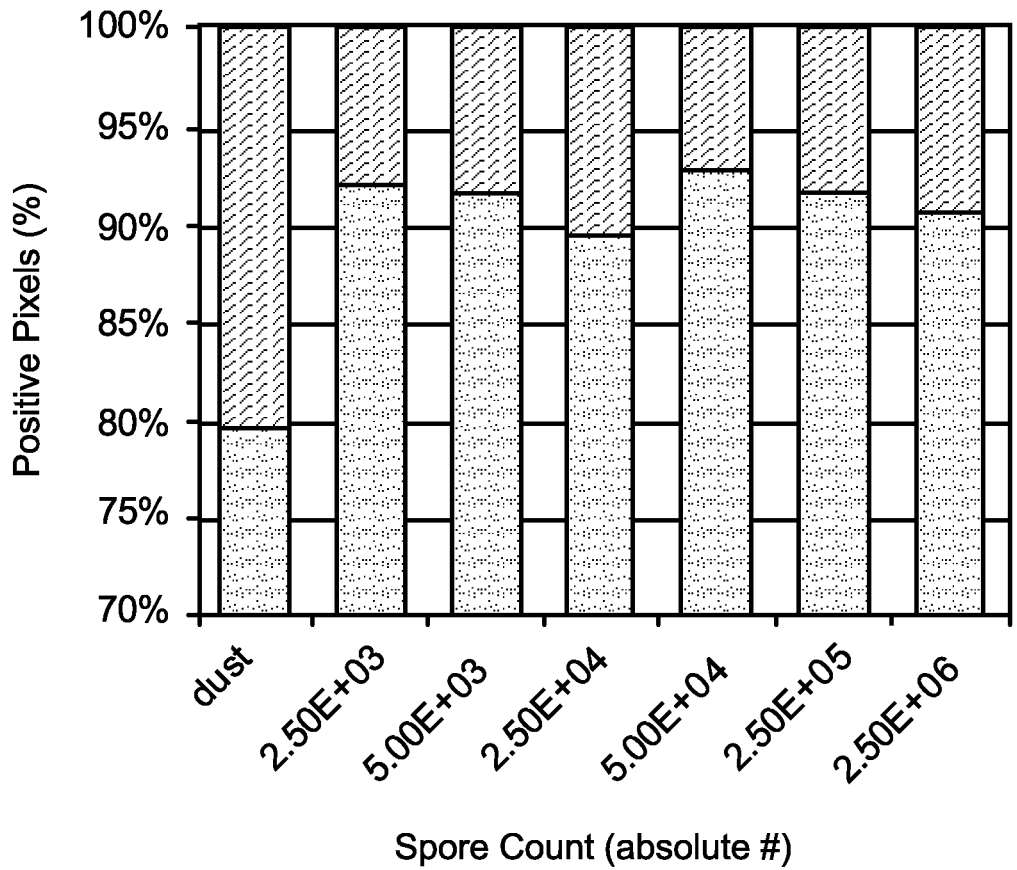
Fig. 4a (distribution of 'background' and 'target' SFPs among positive pixels)

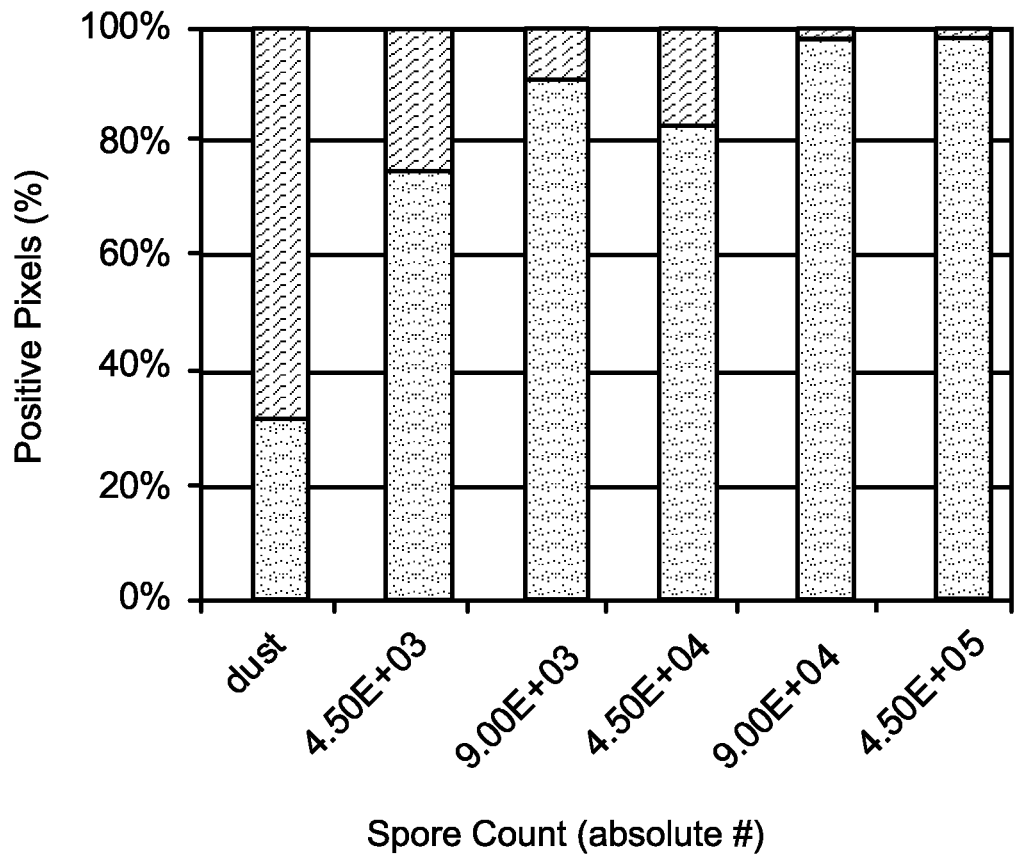
Fig. 4b (distribution of 'background' and 'target' SFPs among positive pixels)
background   targets

HYPER-SPECTRAL IMAGING AND ANALYSIS OF A SAMPLE OF MATTER, FOR IDENTIFYING AND CHARACTERIZING AN OBJECT OF INTEREST THEREIN

RELATED APPLICATIONS

This application is a continuation-in-part (CIP) of U.S. patent application Ser. No. 12/527,206 filed on Aug. 14, 2009, which is a National Phase of PCT Patent Application No. PCT/IL2008/000205 having International Filing Date of Feb. 14, 2008, which claims the benefit of priority from U.S. Provisional Patent Application No. 60/901,320 filed on Feb. 15, 2007. The contents of all the above applications are incorporated by reference as if fully set forth herein.

FIELD AND BACKGROUND OF THE INVENTION

The present invention relates to hyper-spectral imaging and analysis of a sample of matter, and more particularly, to a method for hyper-spectral imaging and analysis of a sample of matter, for identifying and characterizing an object of interest therein. The present invention includes a procedure for preparing a test solution or suspension from a sample of matter, such that the test solution or suspension is particularly suitable for subjecting to hyper-spectral imaging and analysis. The present invention is generally applicable for on-line (e.g., real time or near-real time) or off-line hyper-spectral imaging and analysis of various different types or kinds of samples of matter, wherein the matter, and at least one object of interest therein, are composed or made up of organic or/and inorganic materials or substances, which are in a solid (e.g., particulate) phase, a liquid (e.g., solution or suspension) phase, or/and a gaseous (e.g., aerosol) phase. The present invention provides the capability of achieving the 'ultimate' combination of the highly desirable performance parameters of high accuracy, 'and' high precision (high reproducibility), 'and' high resolution, 'and' high sensitivity, and at high speed (short time scale), all at the same time (i.e., simultaneously), be it during on-line or off-line, in an optimum and highly efficient manner.

An exemplary specific application of the present invention involves on-line (real time or near-real time) or off-line hyper-spectral imaging and analysis of a sample of air (i.e., an air sample), for identifying and characterizing an object of interest therein, wherein the object of interest is a (potentially hazardous) biological agent or a (potentially hazardous) chemical agent. In general, the object of interest (i.e., biological agent or chemical agent) in the air sample is composed or made up of organic or/and inorganic materials or substances, which are in a solid (e.g., particulate) phase, a liquid (e.g., solution or suspension) phase, or/and a gaseous (e.g., aerosol) phase. Preferably, the object of interest (i.e., biological agent or chemical agent) in the air sample is composed or made up of organic or/and inorganic materials or substances, which are in a particulate form solid phase or/and are present (e.g., absorbed or/and adsorbed) on particles of the air sample. The sample of air is collected or obtained (e.g., via a standard type of air sampling or collecting system) from an indoor source of air (e.g., a post office, an airport, a subway station, a shopping mall, a sports arena, or an office building), or from an outdoor source of air. Exemplary biological agents are bacteria, viruses, fungi, and toxins. Exemplary chemical agents are nerve agents (e.g., sarin, tabun, and soman), and chemical poisons (e.g., cyanide compounds, and organophosphate compounds). The object of interest can be a biological agent, such as the (extremely hazardous) spore-forming bacterium *Bacillus anthracis*, which is chemically marked (e.g., via terbium trichloride [$TbCl_3$]), or biologically marked (e.g., via antibodies of an immunoassay technique), as part of the main step (procedure) of preparing a test solution or suspension of the sample of matter, i.e., the air sample, for enabling identification and characterization thereof via hyper-spectral imaging and analysis.

Sample of Matter

A sample of matter generally refers to a relatively small quantity of matter which is representative of, and an example of, (i.e., a sample), of a relatively large, quantity of the matter, where matter generally refers to something (i.e., entity, material, substance) that has mass, occupies volume, and exists as a solid, liquid, gas, or a combination thereof. A sample of matter may also be considered as being a specimen (i.e., example) of the matter. Herein, the term 'object' generally refers to, and is considered equivalent to, and synonymous with, at least part of a given matter, and therefore, that which is present in a sample of the matter. Accordingly, the term 'object' generally refers to, and is considered equivalent to, and synonymous with, at least part of something (i.e., entity, material, substance) that has mass, occupies volume, and exists as a solid, liquid, gas, or a combination thereof, and therefore, that which is present in a sample of matter. Moreover, each object (i.e., at least part of a given matter) is definable and characterizable by a set of a wide variety of numerous possible biological, chemical, or/and physical, properties, characteristics, and behavior.

Analyzing a Sample of Matter

In essentially every field or area of science and technology there are applications which are based on, or involve, the need for on-line (real time or near-real time) or off-line analyzing a sample of matter, for a main purpose or objective of identifying and characterizing at least one object (i.e., entity, material, substance) of interest, usually among a variety of different types or kinds of objects (i.e., entities, materials, substances) of non-interest, in the sample of matter. Such characterization may include determining any number and types or kinds of biological, chemical, or/and physical, properties, characteristics, features, parameters, or/and behavior, of the at least one object of interest in the sample of matter.

There exists a plethora of prior art teachings and practices of a wide variety of different analytical methods and techniques, and associated analytical equipment, instrumentation, hardware, and software, which are suitable for on-line (real time, near-real time) or off-line analyzing a sample of matter. Clearly, many factors, parameters, conditions, criteria, and requirements, are involved that need to be identified, analyzed, considered, accounted for, and possibly tested, in order to properly determine which particular analytical method or technique, and, associated analytical equipment, instrumentation, hardware, and software, are most suitable, alternatively suitable, or optionally suitable, for analyzing a particular sample of matter.

Hyper-spectral imaging and analysis has been established as a highly unique, specialized, and sophisticated, combined spectroscopy and imaging type of analytical method or technique, in the more encompassing field or area of analytical science and technology, involving the sciences and technologies of spectroscopy and imaging. By definition, hyper-spectral imaging and analysis is based on a combination of spectroscopy and imaging theories, principles, and practices, which are exploitable for analyzing samples of matter in a highly unique, specialized, and sophisticated, manner.

Hyper-spectral imaging and analysis, theory, principles, and practices thereof, and, related and associated applications and subjects thereof, such as the more general subject of spectral imaging, are well known and taught about in scientific, technical, and patent, literature, and currently practiced in a wide variety of numerous different fields and areas of science and technology. Several (mostly recent) examples of such teachings and practices are disclosed in references 1-29 (and references cited therein). Selected teachings and practices of hyper-spectral imaging and analysis by the same applicant/assignee of the present invention are disclosed in references 30-36. For the purpose of establishing the scope, meaning, and field(s) or area(s) of application, and meaning, of the present invention, and in understanding problems solved by the present invention, the following background is provided.

Hyper-Spectral Imaging and Analysis

The more highly specialized, complex, and sophisticated, spectroscopic imaging technique of 'hyper-spectral' imaging and analysis, in contrast to the regular or standard spectroscopic imaging technique of 'spectral' imaging and analysis, consists of using a hyper-spectral imaging and analysis system for on-line (real time, near-real time) or off-line generating and collecting (acquiring) hyper-spectral images and spectra (herein, together, generally referred to as hyper-spectral image data and information), and, processing and analyzing the acquired hyper-spectral image data and information. In hyper-spectral imaging, multiple fields of view of a sample of matter are 'hyper-spectrally' scanned and imaged while the sample of matter (containing objects, and components thereof) is exposed to electromagnetic radiation. During the hyper-spectral scanning and imaging there is generating and collecting relatively large numbers (up to the order of millions) of multiple spectral (i.e., hyper-spectral) images, 'one-at-a-time', but, in an extremely fast or rapid sequential manner, of the objects (and components thereof) emitting electromagnetic radiation at a plurality of many wavelengths and frequencies, where the wavelengths and frequencies are associated with different selected (relatively narrow) portions or bands, or bands therein, of an entire hyper-spectrum emitted by the objects (and components thereof). A hyper-spectral imaging and analysis system can be operated in an extremely fast or rapid manner for providing exceptionally highly resolved spectral and spatial data and information of an imaged sample of matter, with high accuracy and high precision (reproducibility), which are fundamentally unattainable by using a regular or standard spectral imaging and analysis system.

In general, when electromagnetic radiation, for example, in the form of light such as that supplied by the sun, or by a man-made imaging type of illuminating or energy source, such as that used during hyper-spectral imaging, is incident upon an object, the electromagnetic radiation is affected by one or more of the biological, chemical, or/and physical, species or components making up the object, by any combination of electromagnetic radiation absorption, diffusion, reflection, diffraction, scattering, or/and transmission, mechanisms. Moreover, an object whose composition includes organic chemical species or components, ordinarily exhibits some degree or extent of fluorescent or/and phosphorescent properties, characteristics, and behavior, when illuminated by some type of electromagnetic radiation or light, such as ultra-violet (UV), visible (VIS), or infrared (IR), types of light. The affected electromagnetic radiation, in the form of diffused, reflected, diffracted, scattered, or/and transmitted, electromagnetic radiation emitted by, or/and emerging from, the object, is directly and uniquely related to the biological, chemical, or/and physical, properties, characteristics, and behavior, of the object, in general, and of the chemical species or components making up the object, in particular, and therefore represents a spectral ('fingerprint' or 'signature') pattern type of identification and characterization of the object.

Accordingly, hyper-spectral images generated by, and collected from, a sample of matter, are correlated with emission spectra of the sample of matter, where the emission spectra correspond to spectral representations in the form of spectral 'fingerprint' or 'signature' pattern types of identification and characterization, of the hyper-spectrally imaged objects (and components thereof) in the sample of matter. Such hyper-spectral image data and information are processed and analyzed by using automatic pattern recognition (APR) or/and optical character recognition (OCR) types of hyper-spectral imaging data and information processing and analysis, for identifying, characterizing, or/and classifying, the physical, chemical, or/and biological, properties, characteristics, and behavior, of the hyper-spectrally imaged objects (and components thereof) in the sample of matter.

Hyper-Spectral Imaging and Analysis of a Sample of Matter

Following provision of a sample of matter, or following obtaining or collecting a sample of matter, analyzing a sample of matter via hyper-spectral imaging and analysis, similar to analyzing a sample of matter by essentially any analytical method or technique, involves three separate, but integrated, general domains or stages of main activities and procedures. In particular, following provision of a sample of matter, or following obtaining or collecting a sample of matter, hyper-spectral imaging and analysis of the sample of matter typically involves the following three separate, but integrated, general domains or stages of main activities and procedures: (i) preparing an appropriate test form (usually, a solid or liquid form) of the sample of matter, which is suitable for being subjected to hyper-spectral imaging and analysis, (ii) generating and collecting hyper-spectral image data and information of the test form of the sample of matter, and (iii) processing and analyzing the generated and collected hyper-spectral image data and information.

In general, each of these three general domains or stages of main activities and procedures of a hyper-spectral imaging and analysis application can be characterized by various different levels or degrees of the following performance parameters: accuracy, precision (reproducibility), sensitivity, resolution, and speed. In any give hyper-spectral imaging and analysis application, the just stated three general domains or stages of main activities and procedures are fully integrated and inter-dependent upon each other.

Performance parameters of accuracy, precision (reproducibility), sensitivity, resolution, or/and speed (time scale), of the first general domain or stage of main activities and procedures of a hyper-spectral imaging and analysis application, i.e., regarding preparation of an appropriate test form of the sample of matter, affect and influence the performance parameters of accuracy, precision (reproducibility), sensitivity, resolution, or/and speed (time scale), of each of the succeeding second and third general domains or stages of main activities and procedures. More specifically, main activities and procedures of preparing an appropriate test form of a sample of matter, affect and influence generating and collecting hyper-spectral image data and information of the test form of the sample of matter, which in turn, affect and influence processing and analyzing the generated and collected hyper-spectral image data and information.

Preparing an Appropriate Test Form of a Sample of Matter

This general domain or stage of main activities and procedures of a hyper-spectral imaging and analysis application involves preparing an appropriate test form of a sample of matter which is suitable for, and compatible with, operation and use of equipment and instrumentation of a given hyper-spectral imaging and analysis system. Typically, an appropriate test form of a sample of matter involves using a relatively small quantity (for example, on the order of microliters (μl)) of the sample of matter, 'as is', in a solid, solution, or suspension, form. Alternatively, according to the actual composition or makeup of the sample of matter (including the objects and components thereof present in the sample of matter), an appropriate test form of a sample of matter may involve dissolving, suspending, or/and mixing, i.e., reformulating, a relatively small quantity of the sample of matter into a solution or suspension form. A portion or aliquot of the solid, solution, or suspension, test form of the sample of matter is then, typically, placed on a clean, inert, metal slide or plate, or, on a clean, inert, plastic (e.g., Teflon®) or glass microscope type slide or plate, which is suitable for functioning as a sample holder in a hyper-spectral imaging and analysis system. The slide or plate (sample holder) with the portion or aliquot of the test solution or suspension of the sample of matter is then appropriately positioned and secured (fixed) upon a three-dimensionally movable (i.e., translational), and optionally, angularly movable (i.e., rotational), examination stage or platform of the hyper-spectral imaging and analysis system.

For the purpose of fully understanding the hereinbelow described significant on-going problems and limitations of hyper-spectral imaging and analysis of a sample of matter, immediately following is a brief description of hyper-spectrally imaged scenes of a test form of a sample of matter, in terms of types, categories, or classes, of objects existing in the hyper-spectrally imaged scenes.

Hyper-Spectrally Imaged Scenes of a Sample of Matter, and Types, Categories, or Classes, of Objects Therein In general, in hyper-spectrally imaged scenes of a test form of a sample of matter (including the objects and components thereof present in the sample of matter), the objects (i.e., entities, materials, substances) can be typed, categorized, or classified, according to two main different types, categories, or classes. Namely, 'objects of non-interest', and 'objects of interest', each of which is basically defined as follows. 'Objects of non-interest' correspond to objects of (present or contained in) a hyper-spectrally imaged scene of the sample of matter which are not of interest to a human operator (observer, viewer, analyzer, or/and controller) of a process involving the sample of matter. 'Objects of interest' correspond to objects of (present or contained in) a hyper-spectrally imaged scene of the sample of matter which are of interest to a human operator of a process involving the sample of matter. For further understanding the significantly different meanings and attributes of objects of non-interest and objects of interest, in the context of the present invention, objects of non-interest are considered as being part of the 'background' of, or within, a hyper-spectrally imaged scene of the sample of matter, whereas objects of interest are considered as being 'targets' of, or within, a hyper-spectrally imaged scene of the sample of matter. Accordingly, in hyper-spectral imaging, individual objects among a plurality, collection, or ensemble, of several objects (i.e., entities, materials, substances) of (present or contained in) a hyper-spectrally imaged scene of a sample of matter, can be typed, categorized, or classified, according to the above stated two main different types, categories, or classes, of objects, i.e., objects of non-interest (i.e., background), and objects of interest (i.e., targets).

Typically, each hyper-spectrally imaged scene of a sample of matter includes or contains a distribution of different relative numbers (i.e., ratios, proportions) of the preceding defined two main different types, categories, or classes, of objects. For example, a given hyper-spectrally imaged scene may include or contain a distribution of a relatively small number of objects of interest (targets), and a relatively large number of objects of non-interest (corresponding to a relatively high or 'noisy' background). Conversely, a given imaged scene may include or contain a distribution of a relatively large number of objects of interest (targets), and a relatively small number of objects of non-interest (corresponding to a relatively low or 'quiet' background).

Moreover, for example, there are many hyper-spectral imaging and analysis applications wherein the majority of hyper-spectrally imaged scenes include or contain a relatively 'exceptionally' small number of objects of interest (targets) compared to a relatively large number of objects of non-interest (high or noisy background). For example, such applications are wherein the number of objects of interest (targets), relative to the number of all objects [of interest (target) and of non-interest (background)] of (present or contained in) a hyper-spectrally imaged scene, corresponds to a ratio or proportion as low as 1% [1 part per hundred (pph)], or $10^{-1}$% [1 part per thousand (ppt)], or $10^{-4}$% [1 part per million (ppm)], $10^{-7}$% [1 part per billion (ppb)], or even as low as $10^{-10}$% [1 part per trillion (pptr)].

In addition to hyper-spectrally imaged scenes including distributions of different relative numbers (ratios, proportions) of the two main different types, categories, or classes, of objects, it is noted that each hyper-spectrally imaged object (i.e., entity, material, substance) is definable and characterizable by a set of a wide variety of numerous possible biological, chemical, or/and physical, properties, characteristics, and behavior. For example, in a given hyper-spectrally imaged scene, there may exist different relative numbers, and types kinds, of objects whose 'hyper-spectral' image data and information (particularly including, for example, emission spectra corresponding to spectral representations in the form of spectral fingerprint or signature pattern types of identification and characterization), are quite similar, or even nearly identical, i.e., barely distinguishable or resolvable, but whose 'biological, chemical, or/and physical' data and information (in terms of properties, characteristics, or/and behavior), are significantly different, and not at all similar or nearly identical, i.e., not at all easily distinguishable or resolvable, or vice versa.

Regardless of the actual distributions of the different relative numbers (i.e., ratios, proportions) of objects of interest (targets) and objects of non-interest (background) in hyper-spectrally imaged scenes of a sample of matter, any hyper-spectral imaging and analysis application ultimately involves the need for identifying, distinguishing, and resolving, the objects of interest (targets) from the objects of non-interest (background) in the hyper-spectrally imaged scenes. This involves the need for identifying, distinguishing, and resolving, the hyper-spectral image data and information of the objects of interest (targets) from the hyper-spectral image data and information of the objects of non-interest (background). Moreover, there is also the need for performing such identifying, distinguishing, and resolving, procedures and operations in relation to the biological, chemical, or/and physical data and information of the objects of interest (targets) and of the objects of non-interest (background), in the hyper-spectrally imaged scenes.

Significant on-Going Problems and Limitations of Hyper-Spectral Imaging and Analysis of a Sample of Matter In general, significant on-going problems and limitations of hyper-spectral imaging and analysis of a sample of matter are usually based on, involve, or/and are associated with, the theoretical or/and practical difficulties and complexities that arise when performing, or attempting to perform, the previously stated three separate, but integrated, general domains or stages, (i), (ii), and (iii), of main activities and procedures, with some combination of the performance parameters of high accuracy, or/and high precision (high reproducibility), or/and high sensitivity, or/and high resolution, or/and at high speed (short time scale), be it during on-line (real time, near-real time) or off-line, in an optimum and highly efficient manner. Exceptional difficulties and complexities arise when performing, or attempting to perform, the general domains or stages, (i), (ii), and (iii), of main activities and procedures, with the 'ultimate' combination of the highly desirable performance parameters of high accuracy, 'and' high precision (high reproducibility), 'and' high sensitivity, 'and' high resolution, 'and' at high speed (short time scale), all at the same time (i.e., simultaneously), be it during on-line (real time, near-real time) or off-line, in an optimum and highly efficient manner.

A main source or origin of difficulties and complexities that arise when performing hyper-spectral imaging and analysis of a sample of matter is the often problematic and complicating spatially or/and temporally varying presence of objects (entities, materials, substances) of non-interest (background) in the sample of matter, directly translating to the corresponding problematic and complicating spatially or/and temporally varying presence of objects of non-interest (background) in the hyper-spectrally imaged scenes of the test form of the sample of matter. The spatially or/and temporally varying presence of objects of non-interest in the sample of matter negatively interferes, to a varying extent or degree (depending upon several interdependent factors), with the hyper-spectral imaging and analysis of the objects (entities, materials, substances) of interest (targets) in the sample of matter. Accordingly, the spatially or/and temporally varying presence of objects of non-interest (background) in the hyper-spectrally imaged scenes of the test form of the sample of matter, negatively interferes, to a varying extent or degree, with the hyper-spectral imaging and analysis of objects of interest (targets) in the hyper-spectrally imaged scenes of the test form of the sample of matter.

The preceding problematic and complicating aspects, regarding the spatially or/and temporally varying presence of objects of non-interest (background), negatively affect and influence generating and collecting hyper-spectral image data and information of the sample of matter, which in turn, negatively affect and influence processing and analyzing the generated and collected hyper-spectral image data and information. Moreover, such problematic and complicating aspects, along with the corresponding negative affects and influences, subsequently make it difficult to achieve high levels of the performance parameters of accuracy, precision (reproducibility), sensitivity, resolution, or/and speed (time scale), of an overall hyper-spectral imaging and analysis application, such as that based on analyzing a sample of matter via hyper-spectral imaging and analysis, for identifying and characterizing an object of interest in the sample.

The preceding problematic and complicating aspects, regarding the spatially or/and temporally varying presence of objects of non-interest (background), which negatively affect and influence hyper-spectral imaging and analysis of a sample of matter, are especially relevant to an application involving on-line (real time or near-real time) or off-line analyzing a sample of air (i.e., an air sample) via hyper-spectral imaging and analysis, for identifying and characterizing an object of interest (target) in the air sample. In particular, wherein such an application, the sample of air can be collected or obtained from an indoor source of air (e.g., a post office, an airport, a subway station, a shopping mall, a sports arena, or an office building) or from an outdoor source of air. In such an application, the interfering objects of non-interest (background) are the numerous different (non-target) components (i.e., entities, materials, substances) present in the air sample. In the air sample, the object of interest (target) can be a (potentially hazardous) biological agent (e.g., a bacterium [such as spore-forming bacterium *Bacillus anthracis*], a virus, a fungus, or a toxin), or a (potentially hazardous) chemical agent (e.g., a nerve agent [e.g., sarin, tabun, or soman], or a chemical poison [e.g., a cyanide compound, or an organophosphate compound]), which is composed or made up of organic or/and inorganic materials or substances, and is preferably in a solid (e.g., particulate) phase.

In the collected sample of air, interfering objects of non-interest (background) originate from the numerous, spatially variable (i.e., varying or changing with position or location) or/and temporally variable (i.e., varying or changing with time) different types and concentrations of (non-target) components (i.e., entities, materials, substances) present in the source of air. The indoor or outdoor source of air typically includes numerous, spatially or/and temporally variable different types and concentrations of (non-target) components, such as dust (fine, dry particles of matter), pollen (fine particulate or powderlike material consisting of pollen grains produced by plants), minerals, non-target types of biological matter (mold (fungi), bacteria), and non-target types of particulate chemical matter. Such (non-target) components in the air source can be in aerosol form, being a gaseous suspension of fine solid or liquid particles which circulate throughout the (indoor or outdoor) air source. Such (non-target) components have relative concentrations which, typically, spatially vary or change (i.e., vary or change with position and location) or/and temporally vary or change (i.e., vary or change with time), depending upon the spatial or/and temporal variations in the local atmospheric environment and weather conditions of the indoor or outdoor source of air, and depending upon the location and time at which the air sample is collected or obtained from the air source. Therefore, a plurality of air samples is expected to have such spatially or/and temporally varying (non-target) components whose relative concentrations vary in accordance with their spatial or/and temporal variation in the source of air from which the air samples are collected or obtained.

In a similar manner, an object of interest (target), such as a (potentially hazardous) biological agent (e.g., a bacterium [such as spore-forming bacterium *Bacillus anthracis]*, a virus, a fungus, or a toxin), or a (potentially hazardous) chemical agent (e.g., a nerve agent [e.g., sarin, tabun, or soman], or a chemical poison [e.g., a cyanide compound, or an organophosphate compound]), which is present in a sample of air collected or obtained from an indoor or outdoor source of air, has a relative concentration which, typically, spatially varies or changes (i.e., varies or changes with position and location) or/and temporally varies or changes (i.e., varies or changes with time), depending upon the spatial or/and temporal variations in the local atmospheric environment and weather conditions of the indoor or outdoor source of air, and depending upon the location and time at which the air sample is collected or obtained from the air source. Therefore, a plurality of air samples is expected to have such a spatially or/and temporally varying object of interest (target) whose relative concentration varies in accordance with its spatial or/and temporal variation in the source of air from which the air samples are collected or obtained.

In such an application, typically, a given hyper-spectrally imaged scene of a test form of an air sample includes or contains a distribution of a relatively small number of the object of interest (target, for example, in the form of a spectrally marked biological or chemical agent), and a relatively large number of the objects of non-interest (high or noisy background, in the form of (non-target) components of the air sample). Moreover, in such an application, typically, the majority of hyper-spectrally imaged scenes include or contain a relatively exceptionally small number of the object of interest (target) compared to a relatively large number of the objects of non-interest (background). For example, wherein the number of the object of interest (target), relative to the number of all objects [of interest (target) and of non-interest (background)] of (present or contained in) a hyper-spectrally imaged scene, corresponds to a ratio or proportion as low as 1% [1 part per hundred (pph)], or $10^{-1}$% [1 part per thousand (ppt)], or $10^{-4}$% [1 part per million (ppm)], $10^{-7}$% [1 part per billion (ppb)], or even as low as $10^{-10}$% [1 part per trillion (pptr)].

Additionally, in such an application, in the hyper-spectrally imaged scenes of a test form of an air sample, each hyper-spectrally imaged object of interest (target, e.g., in the form of a spectrally marked biological or chemical agent) and each hyper-spectrally imaged object of non-interest (background, in the form of (non-target) components of the air sample), is definable and characterizable by a set of a wide variety of numerous possible biological, chemical, or/and physical, properties, characteristics, and behavior. For example, in a given hyper-spectrally imaged scene, there may occur the scenario wherein the object of interest (target, in the form of a spectrally marked biological or chemical agent) and objects of non-interest (background, in the form of (non-target) components of the air sample) exhibit 'hyper-spectral' image data and information (particularly including, for example, emission spectra corresponding to spectral representations in the form of spectral fingerprint or signature pattern types of identification and characterization), which are quite similar, or even nearly identical, i.e., barely distinguishable or resolvable, but whose 'biological, chemical, or/and physical' data and information (in terms of properties, characteristics, or/and behavior), are significantly different, and not at all similar or nearly identical, i.e., not at all easily distinguishable or resolvable, or vice versa.

Regardless of the actual distributions of the different relative numbers (i.e., ratios, proportions) of the object of interest (target, in the form of a spectrally marked biological or chemical agent) and the objects of non-interest (background, in the form of (non-target) components of the air sample), in the hyper-spectrally imaged scenes of the air sample, there ultimately is the need for identifying, distinguishing, and resolving, the object of interest (target, in the form of a spectrally marked biological or chemical agent) from the objects of non-interest (background, in the form of (non-target) components of the air sample) in the hyper-spectrally imaged scenes.

This involves the need for identifying, distinguishing, and resolving, the hyper-spectral image data and information of the object of interest (target, in the form of a spectrally marked biological or chemical agent) from that of the objects of non-interest (background, in the form of (non-target) components of the air sample). Moreover, there is also the need for performing such identifying, distinguishing, and resolving, procedures and operations in relation to the biological, chemical, or/and physical data and information, of the object of interest (target, in the form of a spectrally marked biological or chemical agent) and of the objects of non-interest (background, in the form of (non-target) components of the air sample) in the hyper-spectrally imaged scenes. Furthermore, there is also need for performing such identifying, distinguishing, and resolving, procedures and operations in view of the fact that the hyper-spectrally imaged scenes are generated and collected from air samples wherein the objects of non-interest (background, in the form of (non-target) components of the air sample) and the object of interest (target, in the form of a spectrally marked biological or chemical agent) have relative concentrations that vary in accordance with their spatial or/and temporal variation in the source of air from which the air samples are collected or obtained.

Accordingly, the preceding described problematic and complicating aspects, along with the corresponding negative affects and influences, due to the spatially or/and temporally varying presence of objects of non-interest (background) in a sample of air, make it difficult to achieve high levels of the performance parameters of accuracy, precision (reproducibility), sensitivity, resolution, or/and speed (time scale), of an overall hyper-spectral imaging and analysis application. This is particularly the case for an exemplary specific application involving on-line (real time or near-real time) or off-line hyper-spectral imaging and analysis of a sample of air (i.e., an air sample), for identifying and characterizing an object of interest therein, wherein such an application, the interfering objects of non-interest (background) are the numerous different spatially or/and temporally varying (non-target) components (i.e., entities, materials, substances) present in the air sample, and the object of interest (target) is a (potentially hazardous) biological agent (e.g., a bacterium [such as spore-forming bacterium *Bacillus anthracis]*, a virus, a fungus, or a toxin), or a (potentially hazardous) chemical agent (e.g., a nerve agent [e.g., sarin, tabun, or soman], or a chemical poison [e.g., a cyanide compound, or an organophosphate compound]).

Thus, despite hyper-spectral imaging and analysis being well known and taught about in the prior art and currently practiced in a wide variety of numerous different fields and areas of science and technology, the preceding described problematic and complicating aspects, and corresponding negative affects and influences, which are caused by the spatially or/and temporally varying presence of objects of non-interest (background) in a sample of matter, such as a sample of air, which significantly limit hyper-spectral imaging and analysis of the sample of matter, continue to exist, and need to be overcome.

There is thus a need for, and, it would be highly advantageous and useful to have an invention of a method for hyper-spectral imaging and analysis of a sample of matter, for identifying and characterizing an object of interest therein. There is also need for such an invention which includes a procedure for preparing a test solution or suspension from a sample of matter, such that the test solution or suspension is particularly suitable for subjecting to hyper-spectral imaging and analysis. There is need for such an invention which is generally applicable for on-line (e.g., real time or near-real time) or off-line hyper-spectral imaging and analysis of various different types or kinds of samples of matter, wherein the matter, and at least one object of interest therein, are composed or made up of organic or/and inorganic materials or substances, which are in a solid (e.g., particulate) phase, a liquid (e.g., solution or suspension) phase, or/and a gaseous (e.g., aerosol) phase. Additionally, there is need for such an invention which provides the capability of achieving the 'ultimate' combination of the highly desirable performance parameters of high accuracy, 'and' high precision (high reproducibility), 'and' high sensitivity, 'and' high resolution, 'and' at high speed (short time scale), all at the same time (i.e., simultaneously), be it during on-line or off-line, in an optimum and highly efficient manner.

Furthermore, there is need for such an invention which is particularly implementable in applications involving on-line (real time or near-real time) or off-line hyper-spectral imaging and analysis of a sample of air (i.e., an air sample), for identifying and characterizing an object of interest therein, wherein the object of interest is a (potentially hazardous) biological agent (e.g., a bacterium [such as spore-forming bacterium *Bacillus anthracis*], a virus, a fungus, or a toxin), or a (potentially hazardous) chemical agent (e.g., a nerve agent [e.g., sarin, tabun, or soman], or a chemical poison [e.g., a cyanide compound, or an organophosphate compound]). Moreover, there is need for such an invention where the sample of air is collected or obtained (e.g., via an air sampling or collecting system) from an indoor source of air (e.g., a post office, an airport, a subway station, a shopping mall, a sports arena, or an office building) or from an outdoor source of air. Additionally, there is particular need for such an invention wherein the object of interest can be a biological agent, such as the spore-forming bacterium *Bacillus anthracis*, which is chemically marked (e.g., via terbium trichloride [$TbCl_3$]), or biologically marked (e.g., via antibodies of an immunoassay technique), for enabling identification and characterization thereof via hyper-spectral imaging and analysis.

SUMMARY OF THE INVENTION

The present invention relates to a method for hyper-spectral imaging and analysis of a sample of matter, for identifying and characterizing an object of interest therein. The present invention includes a procedure for preparing a test solution or suspension from a sample of matter, such that the test solution or suspension is particularly suitable for subjecting to hyper-spectral imaging and analysis. The present invention is generally applicable for on-line (e.g., real time or near-real time) or off-line hyper-spectral imaging and analysis of various different types or kinds of samples of matter, wherein the matter, and at least one object of interest therein, are composed or made up of organic or/and inorganic materials or substances, which are in a solid (e.g., particulate) phase, a liquid (e.g., solution or suspension) phase, or/and a gaseous (e.g., aerosol) phase. The present invention provides the capability of achieving the 'ultimate' combination of the highly desirable performance parameters of high accuracy, 'and' high precision (high reproducibility), 'and' high sensitivity, and high resolution, 'and' at high speed (short time scale), all at the same time (i.e., simultaneously), be it during on-line or off-line, in an optimum and highly efficient manner.

Thus, according to an aspect of the present invention, there is provided a method for hyper-spectral imaging and analysis of a sample of matter, for identifying and characterizing an object of interest therein, the method comprising: preparing a test solution or suspension of the sample of matter, the preparing includes adding to the sample of matter a spectral marker specific to the object of interest, such that if the object of interest is present in the test solution or suspension, the object of interest when marked with the spectral marker becomes a hyper-spectrally active target which is hyper-spectrally detectable and identifiable in the test solution or suspension; generating and collecting hyper-spectral image data and information of the test solution or suspension; and, processing and analyzing the hyper-spectral image data and information, for identifying and characterizing the hyper-spectrally active target in the test solution or suspension, thereby identifying and characterizing the object of interest in the sample of matter.

Preparing the test solution or suspension includes adding to the test solution or suspension a background reducing chemical, wherein the background reducing chemical reduces background interfering effects caused by presence of objects of non-interest in the test solution or suspension, during the hyper-spectral imaging and analysis, thereby increasing hyper-spectral detectability of the hyper-spectrally active target in the test solution or suspension, and wherein the generating and collecting the hyper-spectral image data and information of the test solution or suspension includes separately acquiring hyper-spectral image data and information of the objects of non-interest.

According to some embodiments of the present invention, the sample of matter is a sample of air.

According to some embodiments of the present invention, the object of interest is a biological agent or a chemical agent.

According to some embodiments of the present invention, the biological agent is selected from the group consisting of a bacterium, a virus, a fungus, and a toxin.

According to some embodiments of the present invention, the bacterium is spore-forming bacterium *Bacillus anthracis*.

According to some embodiments of the present invention, the chemical agent is selected from the group consisting of a nerve agent, and a chemical poison.

According to some embodiments of the present invention, the spectral marker specific to the object of interest is selected from the group consisting of chemical markers and biological markers.

According to some embodiments of the present invention, the chemical marker is terbium trichloride [$TbCl_3$].

According to some embodiments of the present invention, the biological marker is an antibody of an immunoassay technique.

According to some embodiments of the present invention, the background reducing chemical is selected from the group consisting of solids, and liquids.

According to some embodiments of the present invention, the liquid is an organic liquid.

According to some embodiments of the present invention, the organic liquid is ethylene glycol (monoethylene glycol (MEG) or ethane-1,2-diol) [$HOCH_2CH_2OH$].

According to some embodiments of the present invention, separately acquiring the hyper-spectral image data and information of the objects of non-interest is performed for one or more of the objects of non-interest selected from the group consisting of dust, pollen, minerals, non-target types of biological matter, and non-target types of particulate chemical matter.

According to some embodiments of the present invention, separately acquiring the hyper-spectral image data and information of the objects of non-interest is performed for one or more of the objects of non-interest in a dry form.

According to some embodiments of the present invention, separately acquiring the hyper-spectral image data and information of the objects of non-interest is performed for one or more of the objects of non-interest in a wet form dissolved or suspended in the background reducing chemical, for example, wherein the background reducing chemical is ethylene glycol.

According to some embodiments of the present invention, processing and analyzing the hyper-spectral image data and information includes evaluating a detectability level of the hyper-spectrally active target in the test solution or suspension according to three criteria: (1) area of all positive pixels in a hyper-spectral image expressing characteristic spectral finger prints of light emitted by the hyper-spectrally active target, (2) fluorescence intensity of every positive pixel in the hyper-spectral image that expresses the characteristic spectral finger prints of the hyper-spectrally active target, and (3) relationship between the characteristic spectral finger prints included in the positive pixels of the hyper-spectral image and of a hyper-spectral image database.

According to some embodiments of the present invention, processing and analyzing the hyper-spectral image data and information further includes analyzing the hyper-spectral image for the characteristic spectral finger prints at a one pixel resolution, and calculating total area that subtends all the positive pixels for each hyper-spectral image and concentration of the spectral marker.

According to some embodiments of the present invention, processing and analyzing the hyper-spectral image data and information further includes calculating minimum, maximum, and average intensities of a spectral region around a characteristic emission peak of the hyper-spectrally active target.

According to some embodiments of the present invention, processing and analyzing the hyper-spectral image data and information further includes creating two distinct data bases, wherein a first data base corresponds to all available spectra of the background interfering effects, and a second data base includes all spectra corresponding to the hyper-spectrally active target.

According to some embodiments of the present invention, processing and analyzing the hyper-spectral image data and information further includes comparing spectral finger prints incorporated in the positive pixels of the hyper-spectral image to spectral finger prints from the two distinct data bases, whereby the positive pixels are divided into the hyper-spectrally active target and the background interfering effects, and then correlating, for yielding percentage of the positive pixels corresponding to the hyper-spectrally active target and percentage of the positive pixels corresponding to the background interfering effects.

According to some embodiments of the present invention, the percentages of positive pixels are used in a bar graph for showing distribution of the characteristic spectral finger prints of the hyper-spectrally active target and of the background interfering effects among the positive pixels of the hyper-spectrally active target, as a function of a count of the object of interest.

Following provision of a sample of matter, or following obtaining or collecting a sample of matter, hyper-spectral imaging and analysis of the sample of matter involves the following three separate, but integrated, general domains or stages of main activities and procedures: (i) preparing an appropriate test form (usually, a solid or liquid form) of the sample of matter, which is suitable for being subjected to hyper-spectral imaging and analysis, (ii) generating and collecting hyper-spectral image data and information of the test form of the sample of matter, and (iii) processing and analyzing the generated and collected hyper-spectral image data and information.

Performance parameters of accuracy, precision (reproducibility), sensitivity, resolution, or/and speed (time scale), of the first general domain or stage of main activities and procedures of a hyper-spectral imaging and analysis application, i.e., regarding preparation of an appropriate test form of the sample of matter, affect and influence the performance parameters of accuracy, precision (reproducibility), sensitivity, resolution, or/and speed (time scale), of each of the succeeding second and third general domains or stages of main activities and procedures. More specifically, main activities and procedures of preparing an appropriate test form of a sample of matter, affect and influence generating and collecting hyper-spectral image data and information of the test form of the sample of matter, which in turn, affect and influence processing and analyzing the generated and collected hyper-spectral image data and information.

A main aspect of novelty and inventiveness of the present invention is that in the method for hyper-spectral imaging and analysis of a sample of matter, for identifying and characterizing an object of interest therein, the main step (procedure) of preparing the test solution or suspension of the sample of matter includes the unique and critically important step (procedure) of adding to the test solution or suspension a background reducing chemical. This results in forming the test solution or suspension, wherein the background reducing chemical reduces background interfering effects caused by presence of objects of non-interest in the test solution or suspension, during the hyper-spectral imaging and analysis, thereby increasing hyper-spectral detectability of the hyper-spectrally active target in the test solution or suspension.

An exemplary specific application of the present invention involves on-line (real time or near-real time) or off-line hyper-spectral imaging and analysis of a sample of air (i.e., an air sample), for identifying and characterizing an object of interest therein, wherein the object of interest is a (potentially hazardous) biological agent or a (potentially hazardous) chemical agent. In general, the object of interest (i.e., biological agent or chemical agent) in the air sample is composed or made up of organic or/and inorganic materials or substances, which are in a solid (e.g., particulate) phase, a liquid (e.g., solution or suspension) phase, or/and a gaseous (e.g., aerosol) phase. Preferably, the object of interest (i.e., biological agent or chemical agent) in the air sample is composed or made up of organic or/and inorganic materials or substances, which are in a particulate form solid phase or/and are present (e.g., absorbed or/and adsorbed) on particles of the air sample. The sample of air is collected or obtained (e.g., via a standard type of air sampling or collecting system) from an indoor source of air (e.g., a post office, an airport, a subway station, a shopping mall, a sports arena, or an office building), or from an outdoor source of air. Exemplary biological agents are bacteria, viruses, fungi, and toxins. Exemplary chemical agents are nerve agents (e.g., sarin, tabun, and soman), and chemical poisons (e.g., cyanide compounds, and organophosphate compounds). The object of interest can be a biological agent, such as the (extremely hazardous) spore-forming bacterium *Bacillus anthracis*, which is chemically marked (e.g., via terbium trichloride [$TbCl_3$]), or biologically marked (e.g., via antibodies of an immunoassay technique), as part of the main step (procedure) of preparing a test solution or suspension of the sample of matter, i.e., the air sample, for enabling identification and characterization of the object of interest via hyper-spectral imaging and analysis.

In such an exemplary specific application of the present invention, it was empirically determined (see the Examples hereinbelow) that the background reducing chemical is, preferably, an organic liquid, such as ethylene glycol (equivalently known as monoethylene glycol (MEG) or ethane-1,2-diol) [$HOCH_2CH_2OH$]. The specific type or kind of background reducing chemical, i.e., the ethylene glycol (MEG) [$HOCH_2CH_2OH$], is selected such that the background reducing chemical effectively (i.e., measurably) reduces (decreases) background interfering effects caused by the presence of the numerous, different types of objects of non-interest (background), i.e., (non-target) components, present in the test solution or suspension (particularly the numerous, spatially or/and temporally variable different types and concentrations of (non-target) components, such as dust, pollen, minerals, non-target types of biological matter (mold (fungi), bacteria), and non-target types of particulate chemical matter, which originated from the air sample), during the hyper-spectral imaging and analysis of the test solution or suspension. This results in increasing (enhancing) hyper-spectral detectability of the hyper-spectrally active target (i.e., the {biological agent *Bacillus anthracis* spore (dipicolinic acid [DPA])—terbium trichloride [$TbCl_3$]} complex, or the {biological agent *Bacillus anthracis* spore antigen—antibody} complex) in the test solution or suspension, during the hyper-spectral imaging and analysis of the test solution or suspension. Accordingly, addition of the background reducing chemical, i.e., the ethylene glycol (MEG) [$HOCH_2CH_2OH$], to the test solution or suspension of the air sample results in increasing (enhancing) hyper-spectral detectability of the (target) spore-forming bacterium *Bacillus anthracis*, present in the air sample.

The present invention is implemented by performing steps or procedures, and sub-steps or sub-procedures, in a manner selected from the group consisting of manually, semi-automatically, fully automatically, and a combination thereof, involving use and operation of system units, system sub-units, devices, assemblies, sub-assemblies, mechanisms, structures, components, and elements, and, peripheral equipment, utilities, accessories, chemical reagents, and materials, in a manner selected from the group consisting of manually, semi-automatically, fully automatically, and a combination thereof. Moreover, according to actual steps or procedures, sub-steps or sub-procedures, system units, system sub-units, devices, assemblies, sub-assemblies, mechanisms, structures, components, and elements, and, peripheral equipment, utilities, accessories, chemical reagents, and materials, used for implementing a particular embodiment of the disclosed invention, the steps or procedures, and sub-steps or sub-procedures, are performed by using hardware, software, or/and an integrated combination thereof, and the system units, sub-units, devices, assemblies, sub-assemblies, mechanisms, structures, components, and elements, and, peripheral equipment, utilities, accessories, and materials, operate by using hardware, software, or/and an integrated combination thereof.

BRIEF DESCRIPTION OF THE DRAWINGS

Embodiments of the present invention are herein described, by way of example only, with reference to the accompanying drawings. With specific reference now to the drawings in detail, it is stressed that the particulars shown are by way of example and for purposes of illustrative description of embodiments of the present invention. In this regard, the description taken together with the accompanying drawings make apparent to those skilled in the art how the embodiments of the present invention may be practiced.

In the drawings:

FIG. 1 is a flow diagram of a preferred embodiment of the main steps or procedures of the method for hyper-spectral imaging and analysis of a sample of matter, for identifying and characterizing an object of interest therein, in accordance with the present invention;

FIGS. 2a and 2b are exemplary empirically determined graphical plots (spectra) of Emission Intensity (normalized) as a function of Emission Wavelength (nm) of exemplary dust particles 1 and 2, respectively, in dry form, subjected to hyper-spectral imaging and analysis, showing the spectral fingerprints (SFPs) thereof, as described hereinbelow in Example 1, in accordance with the present invention;

FIG. 3a is an exemplary empirically determined graphical plot (spectrum) of Emission Intensity (normalized) as a function of Emission Wavelength (nm) of a background-only test suspension [containing only objects of non-interest suspended in the exemplary background reducing chemical being the organic liquid ethylene glycol (monoethylene glycol (MEG)); absent of any object of interest or target (i.e., absent of a hyper-spectrally active target being the exemplary {biological agent *Bacillus subtilis* spore (dipicolinic acid [DPA])—terbium trichloride [$TbCl_3$]} complex], subjected to hyper-spectral imaging and analysis, showing the spectral fingerprint (SFP) thereof, as described hereinbelow in Example 3, in accordance with the present invention;

FIG. 3b is an exemplary empirically determined graphical plot (spectrum) of Emission Intensity (normalized) as a function of Emission Wavelength (nm) of a target-containing test suspension [including objects of non-interest, and an exemplary object of interest or target (i.e., a hyper-spectrally active target being the exemplary {biological agent *Bacillus subtilis* spore (dipicolinic acid [DPA])—terbium trichloride [$TbCl_3$]} complex, suspended in the exemplary background reducing chemical being the organic liquid ethylene glycol (monoethylene glycol (MEG))], subjected to hyper-spectral imaging and analysis, showing the spectral fingerprints (SFPs) thereof, as described hereinbelow in Example 3, in accordance with the present invention;

FIG. 4a is an exemplary empirically determined bar graph of Positive Pixels (%) as a function of Spore Count (absolute number) showing distribution of 'background' and 'target' spectral fingerprints (SFPs) among Positive Pixels [of the emission peak (540±5 nm) of an exemplary object of interest or target (i.e., a hyper-spectrally active target being the exemplary {biological agent *Bacillus subtilis* spore (dipicolinic acid [DPA])—terbium trichloride [$TbCl_3$]} complex], as a function of Spore Count, based on hyper-spectral image data and information obtained from FIGS. 3a and 3b and similar experiments, as described hereinbelow in Example 3, in accordance with the present invention; and FIG. 4b is an exemplary empirically determined bar graph of Positive Pixels (%) as a function of Spore Count (absolute number) showing 'reproducibility' of the distribution of background and 'target' spectral fingerprints (SFPs) among Positive Pixels [of the emission peak (540±5 nm) of an exemplary object of interest or target (i.e., a hyper-spectrally active target being the exemplary {biological agent *Bacillus subtilis* spore (dipicolinic acid [DPA])—terbium trichloride [$TbCl_3$]} complex], as a function of Spore Count, based on hyper-spectral image data and information obtained by repeating experiments of Example 3, as described hereinbelow in Example 3, in accordance with the present invention.

DESCRIPTION OF EXEMPLARY EMBODIMENTS

The present invention relates to a method for hyper-spectral imaging and analysis of a sample of matter, for identifying and characterizing an object of interest therein. The present invention includes a procedure for preparing a test solution or suspension from a sample of matter, such that the test solution or suspension is particularly suitable for subjecting to hyper-spectral imaging and analysis. The present invention is generally applicable for on-line (e.g., real time or near-real time) or off-line hyper-spectral imaging and analysis of various different types or kinds of samples of matter, wherein the matter, and at least one object of interest therein, are composed or made up of organic or/and inorganic materials or substances, which are in a solid (e.g., particulate) phase, a liquid (e.g., solution or suspension) phase, or/and a gaseous (e.g., aerosol) phase. The present invention provides the capability of achieving the 'ultimate' combination of the highly desirable performance parameters of high accuracy, 'and' high precision (high reproducibility), 'and' high sensitivity, 'and' high resolution, 'and' at high speed (short time scale), all at the same time (i.e., simultaneously), be it during on-line or off-line, in an optimum and highly efficient manner.

A main aspect of the present invention is provision of a method for hyper-spectral imaging and analysis of a sample of matter, for identifying and characterizing an object of interest therein, the method including the following main steps or procedures, and, components and functionalities thereof: preparing a test solution or suspension of the sample of matter, the preparing includes adding to the sample of matter a spectral marker specific to the object of interest, such that if the object of interest is present in the test solution or suspension, the object of interest when marked with the spectral marker becomes a hyper-spectrally active target which is hyper-spectrally detectable and identifiable in the test solution or suspension; generating and collecting hyper-spectral image data and information of the test solution or suspension; and, processing and analyzing the hyper-spectral image data and information, for identifying and characterizing the hyper-spectrally active target in the test solution or suspension, thereby identifying and characterizing the object of interest in the sample of matter.

Preparing the test solution or suspension includes adding to the test solution or suspension a background reducing chemical, wherein the background reducing chemical reduces background interfering effects caused by presence of objects of non-interest in the test solution or suspension, during the hyper-spectral imaging and analysis, thereby increasing hyper-spectral detectability of the hyper-spectrally active target in the test solution or suspension, and wherein the generating and collecting the hyper-spectral image data and information of the test solution or suspension includes separately acquiring hyper-spectral image data and information of the objects of non-interest.

Following provision of a sample of matter, or following obtaining or collecting a sample of matter, hyper-spectral imaging and analysis of the sample of matter involves the following three separate, but integrated, general domains or stages of main activities and procedures: (i) preparing an appropriate test form (usually, a solid or liquid form) of the sample of matter, which is suitable for being subjected to hyper-spectral imaging and analysis, (ii) generating and collecting hyper-spectral image data and information of the test form of the sample of matter, and (iii) processing and analyzing the generated and collected hyper-spectral image data and information.

Performance parameters of accuracy, precision (reproducibility), sensitivity, resolution, or/and speed (time scale), of the first general domain or stage of main activities and procedures of a hyper-spectral imaging and analysis application, i.e., regarding preparation of an appropriate test form of the sample of matter, affect and influence the performance parameters of accuracy, precision (reproducibility), sensitivity, resolution, or/and speed (time scale), of each of the succeeding second and third general domains or stages of main activities and procedures. More specifically, main activities and procedures of preparing an appropriate test form of a sample of matter, affect and influence generating and collecting hyper-spectral image data and information of the test form of the sample of matter, which in turn, affect and influence processing and analyzing the generated and collected hyper-spectral image data and information.

Embodiments of the present invention include several special technical features, and, aspects of novelty and inventiveness over prior art teachings in the relevant fields and arts of the invention.

A special technical feature of embodiments of the present invention is that in the method for hyper-spectral imaging and analysis of a sample of matter, for identifying and characterizing an object of interest therein, the main step (procedure) of preparing the test solution or suspension of the sample of matter includes the unique and critically important step (procedure) of adding to the test solution or suspension a background reducing chemical. This results in forming the test solution or suspension, wherein the background reducing chemical reduces background interfering effects caused by presence of objects of non-interest in the test solution or suspension, during the hyper-spectral imaging and analysis, thereby increasing hyper-spectral detectability of the hyper-spectrally active target in the test solution or suspension.

An exemplary specific application of the present invention involves on-line (real time or near-real time) or off-line hyper-spectral imaging and analysis of a sample of air (i.e., an air sample), for identifying and characterizing an object of interest therein, wherein the object of interest is a (potentially hazardous) biological agent or a (potentially hazardous) chemical agent. In general, the object of interest (i.e., biological agent or chemical agent) in the air sample is composed or made up of organic or/and inorganic materials or substances, which are in a solid (e.g., particulate) phase, a liquid (e.g., solution or suspension) phase, or/and a gaseous (e.g., aerosol) phase. Preferably, the object of interest (i.e., biological agent or chemical agent) in the air sample is composed or made up of organic or/and inorganic materials or substances, which are in a particulate form solid phase or/and are present (e.g., absorbed or/and adsorbed) on particles of the air sample. The sample of air is collected or obtained (e.g., via a standard type of air sampling or collecting system) from an indoor source of air (e.g., a post office, an airport, a subway station, a shopping mall, a sports arena, or an office building), or from an outdoor source of air. Exemplary biological agents are bacteria, viruses, fungi, and toxins. Exemplary chemical agents are nerve agents (e.g., sarin, tabun, and soman), and chemical poisons (e.g., cyanide compounds, and organophosphates). The object of interest can be a biological agent, such as the (extremely hazardous) spore-forming bacterium *Bacillus anthracis*, which is chemically marked (e.g., via terbium trichloride [$TbCl_3$]), or biologically marked (e.g., via antibodies of an immunoassay technique), for enabling identification and characterization of the object of interest via hyper-spectral imaging and analysis.

In such an exemplary specific application of the present invention, it was empirically determined (see the Examples hereinbelow) that the background reducing chemical is, preferably, an organic liquid, such as ethylene glycol (equivalently known as monoethylene glycol (MEG) or ethane-1,2-diol) [$HOCH_2CH_2OH$]. The specific type or kind of background reducing chemical, i.e., the ethylene glycol (MEG) [$HOCH_2CH_2OH$], is selected such that the background reducing chemical effectively (i.e., measurably) reduces (decreases) background interfering effects caused by the presence of the numerous, different types of objects of non-interest (background), i.e., (non-target) components, present in the test solution or suspension (particularly the numerous, spatially or/and temporally variable different types and concentrations of (non-target) components, such as dust, pollen, minerals, non-target types of biological matter (mold (fungi), bacteria), and non-target types of particulate chemical matter, which originated from the sample of matter), during the hyper-spectral imaging and analysis of the test solution or suspension. This results in increasing (enhancing) hyper-spectral detectability of the hyper-spectrally active target (i.e., the {biological agent *Bacillus anthracis* spore (dipicolinic acid [DPA])—terbium trichloride [$TbCl_3$]} complex], or the {biological agent *Bacillus anthracis* spore antigen—antibody} complex) in the test solution or suspension, during the hyper-spectral imaging and analysis of the test solution or suspension. Accordingly, addition of the background reducing chemical, i.e., the ethylene glycol (MEG) [$HOCH_2CH_2OH$], to the test solution or suspension of the air sample results in increasing (enhancing) hyper-spectral detectability of the (target) spore-forming bacterium *Bacillus anthracis*, present in the air sample.

It is to be understood that the present invention is not limited in its application to the details of the order or sequence, and number, of steps or procedures, sub-steps or sub-procedures, of operation or implementation of the method, or to the details of the equipment, chemical reagents, and materials, used for implementing the method, set forth in the following illustrative description, accompanying drawings, and examples, unless otherwise specifically stated herein. Moreover, although illustrative description, and examples, of the present invention are primarily focused on applications involving a biological agent, wherein the biological agent is, for example, the (extremely hazardous) spore-forming bacterium *Bacillus anthracis*, which is chemically marked (e.g., via terbium trichloride [$TbCl_3$]), or biologically marked (e.g., via antibodies of an immunoassay technique), for enabling identification and characterization thereof via hyper-spectral imaging and analysis, it is to be fully understood that the present invention is also applicable to other biological agents, such as other bacteria, viruses, fungi, and toxins, and the present invention is also applicable to chemical agents, such as nerve agents (e.g., sarin, tabun, and soman), and chemical poisons (e.g., cyanide compounds, and organophosphates). Accordingly, the present invention can be practiced or implemented according to various other alternative embodiments and in various other alternative ways.

It is also to be understood that all technical and scientific words, terms, or/and phrases, used herein throughout the present disclosure have either the identical or similar meaning as commonly understood by one of ordinary skill in the art to which this invention belongs, unless otherwise specifically defined or stated herein. Phraseology, terminology, and, notation, employed herein throughout the present disclosure are for the purpose of description and should not be regarded as limiting.

For example, in the illustrative description of the present invention, there is general reference to the terms 'object' and 'objects', in order to illustrate implementation of the present invention. Herein, the term 'object' as used for illustratively describing the present invention is considered equivalent to, and synonymous with, at least part of an entity, material, substance, or structure, which, singly or in combination with other objects (entities, materials, substances, or structures), typically as part of a scene (defined hereinbelow), is subjected to a hyper-spectral imaging process or technique. In general, such an object is definable and characterizable by a set of a wide variety of numerous possible biological, chemical, or/and physical, properties, characteristics, and behavior. Also, for example, in the illustrative description of the present invention, there is general reference to the term 'marked' in the phrase 'spectrally marked', and, to the term 'marker' in the phrases 'spectral marker', 'chemical marker', and 'biological marker', in order to illustrate implementation of the present invention. As used herein, the terms 'marked' and 'marker' are considered equivalent to, and synonymous with, the terms 'labeled' and 'label', respectively. Thus, herein, the phrases 'spectrally marked', 'spectral marker', 'chemical marker', and 'biological marker', are considered equivalent to, and synonymous with, the phrases 'spectrally labeled', 'spectral label', 'chemical label', and 'biological label', respectively.

Moreover, all technical and scientific words, terms, or/and phrases, introduced, defined, described, or/and exemplified, in the above Field and Background section, are equally or similarly applicable in the illustrative description of the preferred embodiments, examples, and appended claims, of the present invention. Immediately following are selected definitions and exemplary usages of words, terms, or/and phrases, which are used throughout the illustrative description of the preferred embodiments, examples, and appended claims, of the present invention, and are especially relevant for understanding thereof.

Each of the following terms: 'includes', 'including', 'has', 'having', 'comprises', and 'comprising', and, their derivatives and conjugates, means 'including, but not limited to'.

Each of the following terms written in singular grammatical form: 'a', 'an', and 'the', may also refer to, and encompass, a plurality of the stated entity or object, unless otherwise specifically defined or stated herein, or, unless the context clearly dictates otherwise. For example, the phrases 'an object', 'a target', 'a component', and 'an element', may also refer to, and encompass, a plurality of objects, a plurality of targets, a plurality of components, and a plurality of elements, respectively.

The term 'about' refers to ±10% of the stated numerical value.

The phrase 'room temperature' refers to a temperature in a range of between about 20° C. and about 25° C.

Throughout the illustrative description of the embodiments, the examples, and the appended claims, of the present invention, a numerical value of a parameter, feature, object, or dimension, may be stated or described in terms of a numerical range format. It is to be fully understood that the stated numerical range format is provided for illustrating implementation of the present invention, and is not to be understood or construed as inflexibly limiting the scope of the present invention.

Accordingly, a stated or described numerical range also refers to, and encompasses, all possible sub-ranges and individual numerical values (where a numerical value may be expressed as a whole, integral, or fractional number) within that stated or described numerical range. For example, a stated or described numerical range 'from 1 to 6' also refers to, and encompasses, all possible sub-ranges, such as 'from 1 to 3', 'from 1 to 4', 'from 1 to 5', 'from 2 to 4', 'from 2 to 6', 'from 3 to 6', etc., and individual numerical values, such as '1', '1.3', '2', '2.8', '3', '3.5', '4', '4.6', '5', '5.2', and '6', within the stated or described numerical range of 'from 1 to 6'. This applies regardless of the numerical breadth, extent, or size, of the stated or described numerical range.

Moreover, for stating or describing a numerical range, the phrase 'in a range of between about a first numerical value and about a second numerical value', is considered equivalent to, and meaning the same as, the phrase 'in a range of from about a first numerical value to about a second numerical value', and, thus, the two equivalently meaning phrases may be used interchangeably. For example, for stating or describing the numerical range of room temperature, the phrase 'room temperature refers to a temperature in a range of between about 20° C. and about 25° C.', is considered equivalent to, and meaning the same as, the phrase 'room temperature refers to a temperature in a range of from about 20° C. to about 25° C.'.

Steps or procedures, sub-steps or sub-procedures, and, equipment and materials, system units, system sub-units, devices, assemblies, sub-assemblies, mechanisms, structures, components, elements, and configurations, and, peripheral equipment, utilities, accessories, chemical reagents, and materials, as well as operation and implementation, of exemplary preferred embodiments, alternative preferred embodiments, specific configurations, and, additional and optional aspects, characteristics, or features, thereof, according to the present invention, are better understood with reference to the following illustrative description and accompanying drawings.

According to a main aspect of the present invention, there is provision of a method for hyper-spectral imaging and analysis of a sample of matter, for identifying and characterizing an object of interest therein.

Referring now to the drawings, FIG. 1 is a flow diagram of a preferred embodiment of the main steps or procedures, and, components and functionalities thereof, of the method for hyper-spectral imaging and analysis of a sample of matter, for identifying and characterizing an object of interest therein. Accordingly, the method includes the following main steps or procedures, and, components and functionalities thereof: preparing a test solution or suspension of the sample of matter, the preparing includes adding to the sample of matter a spectral marker specific to the object of interest, such that if the object of interest is present in the test solution or suspension, the object of interest when marked with the spectral marker becomes a hyper-spectrally active target which is hyper-spectrally detectable and identifiable in the test solution or suspension; generating and collecting hyper-spectral image data and information of the test solution or suspension; and, processing and analyzing the hyper-spectral image data and information, for identifying and characterizing the hyper-spectrally active target in the test solution or suspension, thereby identifying and characterizing the object of interest in the sample of matter.

The method is characterized in that the step of preparing the test solution or suspension includes adding to the test solution or suspension a background reducing chemical, wherein the background reducing chemical reduces background interfering effects caused by presence of objects of non-interest in the test solution or suspension, during the hyper-spectral imaging and analysis, thereby increasing hyper-spectral detectability of the hyper-spectrally active target in the test solution or suspension.

Applicable Types or Kinds, and Forms, of the Sample of Matter

In general, the present invention is applicable to essentially any type or kind, and form, of sample of matter. The sample of matter is generally a relatively small quantity of matter which is representative of, and an example of, (i.e., a sample), of a relatively large, quantity of the matter, where the matter is generally something (i.e., entity, material, substance) that has mass, occupies volume, and exists as a solid, liquid, gas, or a combination thereof. The sample of matter may also be considered as being a specimen (i.e., example) of the matter. The sample of matter is composed or made up of any number, and type or kind, of objects, wherein each object generally refers to, and is considered equivalent to, and synonymous with, at least part of the matter, and therefore, that which is present in a sample of the matter. Accordingly, each object generally refers to, and is considered equivalent to, and synonymous with, at least part of something (i.e., entity, material, substance) that has mass, occupies volume, and exists as a solid, liquid, gas, or a combination thereof. Moreover, each object (i.e., at least part of the matter) is definable and characterizable by a set of a wide variety of numerous possible biological, chemical, or/and physical, properties, characteristics, and behavior.

>For a Sample of Air (Air Sample) Containing Numerous Different Spatially or/and Temporally Varying Interfering Objects of Non-Interest (Background), and a Biological Agent or Chemical Agent Type of Object of Interest (Target)<

In an exemplary specific embodiment of the present invention, the sample of matter is a sample of air (i.e., an air sample). Accordingly, an exemplary specific embodiment of the present invention involves on-line (real time or near-real time) or off-line hyper-spectral imaging and analysis of a sample of air (i.e., an air sample), for identifying and characterizing an object of interest therein.

An exemplary specific application of the present invention involves on-line (real time or near-real time) or off-line hyper-spectral imaging and analysis of a sample of air (i.e., an air sample), for identifying and characterizing an object of interest therein, wherein the object of interest is a biological agent or a chemical agent. In general, the object of interest (i.e., biological agent or chemical agent) in the air sample is composed or made up of organic or/and inorganic materials or substances, which are in a solid (e.g., particulate) phase, a liquid (e.g., solution or suspension) phase, or/and a gaseous (e.g., aerosol) phase. Preferably, the object of interest (i.e., biological agent or chemical agent) in the air sample is composed or made up of organic or/and inorganic materials or substances, which are in a particulate form solid phase or/and are present (e.g., absorbed or/and adsorbed) on particles of the air sample. The sample of air is collected or obtained (e.g., via a standard type of air sampling or collecting system) from an indoor source of air (e.g., a post office, an airport, a subway station, a shopping mall, a sports arena, or an office building), or from an outdoor source of air. Exemplary biological agents are bacteria, viruses, fungi, and toxins. Exemplary chemical agents are nerve agents (e.g., sarin, tabun, and soman), and chemical poisons (e.g., cyanide compounds, and organophosphate compounds). The object of interest can be a biological agent, such as the spore-forming bacterium *Bacillus anthracis,* which is chemically marked (e.g., via terbium trichloride $[TbCl_3]$), or biologically marked (e.g., via antibodies of an immunoassay technique), as part of the main step (procedure) of preparing a test solution or suspension of the sample of matter, i.e., the air sample, for enabling identification and characterization of the object of interest via hyper-spectral imaging and analysis.

Types, Categories, or Classes, of Objects in the Sample of Matter

In general, in the sample of matter (including the objects and components thereof present in the sample of matter), the objects (i.e., entities, materials, substances) are typed, categorized, or classified, according to two main different types, categories, or classes. Namely, 'objects of non-interest', and 'objects of interest', each of which is basically defined as follows. 'Objects of non-interest' correspond to objects of (present or contained in) the sample of matter which are not of interest to a human operator (observer, viewer, analyzer, or/and controller) of a process involving the sample of matter. 'Objects of interest' correspond to objects of (present or contained in) the sample of matter which are of interest to a human operator of a process involving the sample of matter. For further understanding the significantly different meanings and attributes of objects of non-interest and objects of interest, in the context of the present invention, objects of non-interest are considered as being part of the 'background' of, or within, the sample of matter, whereas objects of interest are considered as being 'targets' of, or within, the sample of matter. Accordingly, individual objects among a plurality, collection, or ensemble, of several objects (i.e., entities, materials, substances) of (present or contained in) the sample of matter, are typed, categorized, or classified, according to the above stated two main different types, categories, or classes, of objects, i.e., objects of non-interest (i.e., background), and objects of interest (i.e., targets).

Typically, the sample of matter includes or contains a distribution of different relative numbers (i.e., ratios, proportions) of the preceding defined two main different types, categories, or classes, of objects. For example, the sample of matter may include or contain a distribution of a relatively small number of objects of interest (targets), and a relatively large number of objects of non-interest (corresponding to a relatively high or 'noisy' background). Conversely, the sample of matter may include or contain a distribution of a relatively large number of objects of interest (targets), and a relatively small number of objects of non-interest (corresponding to a relatively low or 'quiet' background).

Moreover, for example, there are many applications of the present invention wherein the sample of matter includes or contains a relatively 'exceptionally' small number of objects of interest (targets) compared to a relatively large number of objects of non-interest (high or noisy background). For example, such applications are wherein the number of objects of interest (targets), relative to the number of all objects [of interest (target) and of non-interest (background)] of (present or contained in) the sample of matter, corresponds to a ratio or proportion as low as 1% [1 part per hundred (pph)], or $10^{-1}$% [1 part per thousand (ppt)], or $10^{-4}$% [1 part per million (ppm)], $10^{-7}$% [1 part per billion (ppb)], or even as low as $10^{-10}$% [1 part per trillion (pptr)].

In addition to the sample of matter including distributions of different relative numbers (ratios, proportions) of the two main different types, categories, or classes, of objects, it is noted that, as indicated hereinabove, each object (i.e., entity, material, substance) is definable and characterizable by a set of a wide variety of numerous possible biological, chemical, or/and physical, properties, characteristics, and behavior. For example, in the sample of matter, there may exist different types, kinds, and numbers, of objects whose 'hyper-spectral' image data and information (including, for example, emission spectra corresponding to spectral representations in the form of spectral fingerprint (herein, abbreviated, and also referred to, as SFP) or signature pattern types of identification and characterization), are quite similar, or even nearly identical, i.e., barely distinguishable or resolvable, but whose 'biological, chemical, or/and physical' data and information (in terms of properties, characteristics, or/and behavior), are significantly different, and not at all similar or nearly identical, i.e., not at all easily distinguishable or resolvable, or vice versa.

Regardless of the actual distributions of the different relative numbers (i.e., ratios, proportions) of objects of interest (targets) and objects of non-interest (background) in the sample of matter, any application of the present invention ultimately involves the need for identifying, distinguishing, and resolving, the objects of interest (targets) from the objects of non-interest (background) in the sample of matter. This involves the need for identifying, distinguishing, and resolving, the hyper-spectral image data and information of the objects of interest (targets) from the hyper-spectral image data and information of the objects of non-interest (background). Moreover, there is also the need for performing such identifying, distinguishing, and resolving, procedures and operations in relation to the biological, chemical, or/and physical data and information of the objects of interest (targets) and of the objects of non-interest (background), in the sample of matter.

A main source or origin of difficulties and complexities that arise when performing hyper-spectral imaging and analysis of a sample of matter is the often problematic and complicating spatially or/and temporally varying presence of objects (entities, materials, substances) of non-interest (background) in the sample of matter, directly translating to the corresponding problematic and complicating spatially or/and temporally varying presence of objects of non-interest (background) in the hyper-spectrally imaged scenes of the test form of the sample of matter. The spatially or/and temporally varying presence of objects of non-interest in the sample of matter negatively interferes, to a varying extent or degree (depending upon several interdependent factors), with the hyper-spectral imaging and analysis of the objects (entities, materials, substances) of interest (targets) in the sample of matter. Accordingly, the spatially or/and temporally varying presence of objects of non-interest (background) in the hyper-spectrally imaged scenes of the test form of the sample of matter, negatively interferes, to a varying extent or degree, with the hyper-spectral imaging and analysis of objects of interest (targets) in the hyper-spectrally imaged scenes of the test form of the sample of matter.

The preceding problematic and complicating aspects, regarding the spatially or/and temporally varying presence of objects of non-interest (background), negatively affect and influence generating and collecting hyper-spectral image data and information of the sample of matter, which in turn, negatively affect and influence processing and analyzing the generated and collected hyper-spectral image data and information. Moreover, such problematic and complicating aspects, along with the corresponding negative affects and influences, subsequently make it difficult to achieve high levels of the performance parameters of accuracy, precision (reproducibility), sensitivity, resolution, or/and speed (time scale), of an overall hyper-spectral imaging and analysis application, such as that based on analyzing a sample of matter via hyper-spectral imaging and analysis, for identifying and characterizing an object of interest in the sample.

>For a Sample of Air (Air Sample) Containing Numerous Different Spatially or/and Temporally Varying Interfering Objects of Non-Interest (Background), and a Biological Agent or Chemical Agent Type of Object of Interest (Target)<

The preceding problematic and complicating aspects, regarding the spatially or/and temporally varying presence of objects of non-interest (background), which negatively affect and influence hyper-spectral imaging and analysis of a sample of matter, are especially relevant to an application of the present invention, involving on-line (real time or near-real time) or off-line analyzing a sample of air (i.e., an air sample) via hyper-spectral imaging and analysis, for identifying and characterizing an object of interest (target) in the air sample. In particular, wherein such an application, the sample of air is collected or obtained (e.g., via a standard type of air sampling or collecting system) from an indoor source of air (e.g., a post office, an airport, a subway station, a shopping mall, a sports arena, or an office building) or from an outdoor source of air.

In such an application, the interfering objects of non-interest (background) are the numerous different (non-target) components (i.e., entities, materials, substances) present in the air sample. In the air sample, the object of interest (target)

is a (potentially hazardous) biological agent (e.g., bacterium [such as (the extremely hazardous) spore-forming bacterium *Bacillus anthracis*], a virus, a fungus, or a toxin), or a (potentially hazardous) chemical agent (e.g., a nerve agent [e.g., sarin, tabun, or soman], or a chemical poison [e.g., a cyanide compound, or an organophosphate compound]), which is composed or made up of organic or/and inorganic materials or substances, and is preferably in a solid (e.g., particulate) phase.

In the collected sample of air, interfering objects of non-interest (background) originate from the numerous, spatially variable (i.e., varying or changing with position or location) or/and temporally variable (i.e., varying or changing with time) different types and concentrations of (non-target) components (i.e., entities, materials, substances) present in the source of air. The indoor or outdoor source of air typically includes numerous, spatially or/and temporally variable different types and concentrations of (non-target) components, such as dust (fine, dry particles of matter), pollen (fine particulate or powderlike material consisting of pollen grains produced by plants), minerals, non-target types of biological matter (mold (fungi), bacteria), and non-target types of particulate chemical matter. Such (non-target) components in the air source can be in aerosol form, being a gaseous suspension of fine solid or liquid particles which circulate throughout the (indoor or outdoor) air source. Such (non-target) components have relative concentrations which, typically, spatially vary or change (i.e., vary or change with position and location) or/and temporally vary or change (i.e., vary or change with time), depending upon the spatial or/and temporal variations in the local atmospheric environment and weather conditions of the indoor or outdoor source of air, and depending upon the location and time at which the air sample is collected or obtained from the air source. Therefore, a plurality of air samples is expected to have such spatially or/and temporally varying (non-target) components whose relative concentrations vary in accordance with their spatial or/and temporal variation in the source of air from which the air samples are collected or obtained.

In a similar manner, the object of interest (target), such as a (potentially hazardous) biological agent (e.g., a bacterium [such as spore-forming bacterium *Bacillus anthracis]*, a virus, a fungus, or a toxin), or a (potentially hazardous) chemical agent (e.g., a nerve agent [e.g., sarin, tabun, or soman], or a chemical poison [e.g., a cyanide compound, or an organophosphate compound]), which is present in a sample of air collected or obtained from an indoor or outdoor source of air, has a relative concentration which, typically, spatially varies or changes (i.e., varies or changes with position and location) or/and temporally varies or changes (i.e., varies or changes with time), depending upon the spatial or/and temporal variations in the local atmospheric environment and weather conditions of the indoor or outdoor source of air, and depending upon the location and time at which the air sample is collected or obtained from the air source. Therefore, a plurality of air samples is expected to have such a spatially or/and temporally varying object of interest (target) whose relative concentration varies in accordance with its spatial or/and temporal variation in the source of air from which the air samples are collected or obtained.

In such an application of the present invention, typically, a given hyper-spectrally imaged scene of a test form of an air sample includes or contains a distribution of a relatively small number of the object of interest (target, for example, in the form of a spectrally marked biological or chemical agent), and a relatively large number of the objects of non-interest (high or noisy background, in the form of (non-target) components of the air sample). Moreover, in such an application, typically, the majority of hyper-spectrally imaged scenes include or contain a relatively exceptionally small number of the object of interest (target) compared to a relatively large number of the objects of non-interest (background). For example, wherein the number of the object of interest (target), relative to the number of all objects [of interest (target) and of non-interest (background)] of (present or contained in) a hyper-spectrally imaged scene, corresponds to a ratio or proportion as low as 1% [1 part per hundred (pph)], or $10^{-1}$% [1 part per thousand (ppt)], or $10^{-4}$% [1 part per million (ppm)], $10^{-7}$% [1 part per billion (ppb)], or even as low as $10^{-10}$% [1 part per trillion (pptr)].

Additionally, in such an application of the present invention, in the hyper-spectrally imaged scenes of a test form of an air sample, each hyper-spectrally imaged object of interest (target, e.g., in the form of a spectrally marked biological or chemical agent) and each hyper-spectrally imaged object of non-interest (background, in the form of (non-target) components of the air sample), is definable and characterizable by a set of a wide variety of numerous possible biological, chemical, or/and physical, properties, characteristics, and behavior. For example, in a given hyper-spectrally imaged scene, there may occur the scenario wherein the object of interest (target, in the form of a spectrally marked biological or chemical agent) and objects of non-interest (background, in the form of (non-target) components of the air sample) exhibit 'hyper-spectral' image data and information (particularly including, for example, emission spectra corresponding to spectral representations in the form of spectral fingerprint (SFP) or signature pattern types of identification and characterization), which are quite similar, or even nearly identical, i.e., barely distinguishable or resolvable, but whose 'biological, chemical, or/and physical' data and information (in terms of properties, characteristics, or/and behavior), are significantly different, and not at all similar or nearly identical, i.e., not at all easily distinguishable or resolvable, or vice versa.

Regardless of the actual distributions of the different relative numbers (i.e., ratios, proportions) of the object of interest (target, in the form of a spectrally marked biological or chemical agent) and the objects of non-interest (background, in the form of (non-target) components of the air sample), in the hyper-spectrally imaged scenes of the air sample, there ultimately is the need for identifying, distinguishing, and resolving, the object of interest (target, in the form of a spectrally marked biological or chemical agent) from the objects of non-interest (background, in the form of (non-target) components of the air sample) in the hyper-spectrally imaged scenes.

This involves the need for identifying, distinguishing, and resolving, the hyper-spectral image data and information of the object of interest (target, in the form of a spectrally marked biological or chemical agent) from that of the objects of non-interest (background, in the form of (non-target) components of the air sample). Moreover, there is also the need for performing such identifying, distinguishing, and resolving, procedures and operations in relation to the biological, chemical, or/and physical data and information, of the object of interest (target, in the form of a spectrally marked biological or chemical agent) and of the objects of non-interest (background, in the form of (non-target) components of the air sample) in the hyper-spectrally imaged scenes. Furthermore, there is also need for performing such identifying, distinguishing, and resolving, procedures and operations in view of the fact that the hyper-spectrally imaged scenes are generated and collected from air samples wherein the objects of non-interest (background, in the form of (non-target) components of the air sample) and the object of interest (target, in the form of a spectrally marked biological or chemical agent) have relative concentrations that vary in accordance with their spatial or/and temporal variation in the source of air from which the air samples are collected or obtained.

Accordingly, the preceding described problematic and complicating aspects, along with the corresponding negative affects and influences, due to the spatially or/and temporally varying presence of objects of non-interest (background) in a sample of air, make it difficult to achieve high levels of the performance parameters of accuracy, precision (reproducibility), sensitivity, resolution, or/and speed (time scale), of an overall hyper-spectral imaging and analysis application. This is particularly the case for an exemplary specific application involving on-line (real time or near-real time) or off-line hyper-spectral imaging and analysis of a sample of air (i.e., an air sample), for identifying and characterizing an object of interest therein, wherein such an application, the interfering objects of non-interest (background) are the numerous different spatially or/and temporally varying (non-target) components (i.e., entities, materials, substances) present in the air sample, and the object of interest (target) is a (potentially hazardous) biological agent (e.g., a bacterium [such as spore-forming bacterium *Bacillus anthracis]*, a virus, a fungus, or a toxin), or a (potentially hazardous) chemical agent (e.g., a nerve agent [e.g., sarin, tabun, or soman], or a chemical poison [e.g., a cyanide compound, or an organophosphate compound]).

Implementation of the present invention enables overcoming the preceding described problematic and complicating aspects, and corresponding negative affects and influences, which are caused by the spatially or/and temporally varying presence of objects of non-interest (background) in a sample of matter, such as a sample of air, which significantly limit hyper-spectral imaging and analysis of the sample of matter.

Preparing a Test Solution or Suspension of the Sample of Matter

In this main step (procedure), there is preparing a test solution or suspension of the sample of matter. The test solution or suspension of the sample of matter is prepared in a form which is suitable for, and compatible with, operation and use of equipment and instrumentation of a given hyper-spectral imaging and analysis system.

Following provision of the sample of matter, or following obtaining or collecting the sample of matter, there is preparing a test solution or suspension of the sample of matter. Preferably, there is dissolving, suspending, or/and mixing, i.e., reformulating, a relatively small quantity of the sample of matter into a solution or suspension form, for forming a test solution or suspension of the sample of matter. The procedure of dissolving, suspending, or/and mixing, i.e., reformulating, is performed using a liquid, for example, distilled water, or other liquid, which is suitable for dissolving or suspending the different types of objects of non-interest (background), i.e., (non-target) components, present in the sample of matter, and which is suitable for dissolving or suspending the object of interest (target), i.e., (target) component, present in the sample of matter.

The specific liquid used for dissolving, suspending, or/and mixing, i.e., reformulating, the small quantity of the sample of matter into a test solution or suspension, is selected whereby the liquid minimally affects hyper-spectral imaging and analysis of the numerous, different types of objects of non-interest (background), i.e., (non-target) components, present in the sample of matter (and subsequently present in the test solution or suspension), and whereby the liquid minimally affects hyper-spectral imaging and analysis of the object of interest (target), i.e., (target) component, present in the sample of matter (and subsequently present in the test solution or suspension).

Adding to the Sample of Matter a Spectral Marker Specific to the Object of Interest (Target)

Often, an object of interest (target), i.e., (target) component, present in the sample of matter, by itself, is not 'spectrally' active, i.e., the object of interest (target) exhibits an insufficiently detectable or/and insufficiently measurable degree or extent of luminescent (i.e., fluorescent or/and phosphorescent) properties, characteristics, and behavior, when illuminated by electromagnetic radiation or light, such as ultra-violet (UV), visible (VIS), or infrared (IR), types of light.

Thus, with reference to FIG. 1, the main step (procedure) of preparing a test solution or suspension of the sample of matter includes the step (procedure) of adding to the sample of matter, a spectral marker specific to the object of interest (target), such that if the object of interest (target) is present in the test solution or suspension, the object of interest (target) when marked with the spectral marker becomes a hyper-spectrally active target which is hyper-spectrally detectable and identifiable in the test solution or suspension.

In general, the spectral marker is added to the sample of matter immediately before or after, dissolving, suspending, or/and mixing, i.e., reformulating, the relatively small quantity of the sample of matter into a solution or suspension form.

The spectral marker is, in general, a chemical type of spectral marker, or a biological type of spectral marker. A suitable chemical type of spectral marker is, in general, a chemical specie which interacts with (i.e., spectrally marks) the object of interest (target) for forming an {object of interest—chemical marker} complex which exhibits a detectable and measurable degree or extent of (spectral) luminescent (i.e., fluorescent or/and phosphorescent) properties, characteristics, and behavior, when illuminated by different types of electromagnetic radiation or light, such as ultra-violet (UV), visible (VIS), or infrared (IR), types of light. A suitable biological type of spectral marker is, in general, a biological specie which interacts with (i.e., spectrally marks) the object of interest (target) for forming an {object of interest—biological marker} complex which exhibits some degree or extent of (spectral) luminescent (i.e., fluorescent or/and phosphorescent) properties, characteristics, and behavior, when illuminated by different types of electromagnetic radiation or light, such as ultra-violet (UV), visible (VIS), or infrared (IR), types of light.

In any case of the object of interest (target) being spectrally marked with the chemical type of spectral marker, or with the biological type of spectral marker, the formed {object of interest—chemical marker} complex, or {object of interest—biological marker} complex, respectively, becomes a hyper-spectrally active target which is hyper-spectrally detectable and identifiable in the test solution or suspension of the sample of matter, when the test solution or suspension is subjected to hyper-spectral imaging and analysis, thereby enabling identifying and characterizing the object of interest in the sample of matter.

Adding to the Test Solution or Suspension a Background Reducing Chemical

As shown in FIG. 1, the main step (procedure) of preparing the test solution or suspension of the sample of matter includes the unique and critically important step (procedure) of adding to the test solution or suspension a background reducing chemical. The background reducing chemical reduces background interfering effects caused by presence of objects of non-interest in the test solution or suspension, during the hyper-spectral imaging and analysis of the test solution or suspension, thereby increasing hyper-spectral detectability of the hyper-spectrally active target in the test solution or suspension, and thus enhancing identification and characterization of the object of interest in the sample of matter.

The background reducing chemical is, in general, any type or kind of chemical which is composed or made up of one or more organic or/and inorganic materials or substances, which is/are in a solid (e.g., particulate) phase, a liquid (e.g., solution or suspension) phase, or a combination thereof.

The specific type or kind of background reducing chemical is selected such that the background reducing chemical effectively (i.e., measurably) reduces (decreases) background interfering effects caused by the presence of the numerous, different types of objects of non-interest (background), i.e., (non-target) components, in the test solution or suspension (particularly those objects of non-interest (background), i.e., (non-target) components, which originated from the sample of matter), during the hyper-spectral imaging and analysis of the test solution or suspension. This results in increasing (enhancing) hyper-spectral detectability of the hyper-spectrally active target in the test solution or suspension, during the hyper-spectral imaging and analysis of the test solution or suspension. Accordingly, addition of the background reducing chemical to the test solution or suspension of the sample of matter results in increasing (enhancing) hyper-spectral detectability of the object of interest (target), i.e., (target) component, present in the sample of matter.

The background reducing chemical, following addition to the test solution or suspension, and during the hyper-spectral imaging of the test solution or suspension, exhibits some combination of the following two main modes of behavior.

First, the background reducing chemical selectively, 'physicochemically interacts', during the hyper-spectral imaging, with a major portion of the numerous, different types of objects of non-interest (background), i.e., (non-target) components, present in the test solution or suspension (particularly those objects of non-interest (background), i.e., (non-target) components, which originated from the sample of matter), in a manner which effectively (i.e., measurably) reduces (decreases) their (spectral) luminescent (i.e., fluorescent or/and phosphorescent) properties, characteristics, and behavior. During the hyper-spectral imaging, the background reducing chemical may or may not effectively (i.e., measurably) 'chemically react', but at least to some extent 'physically interacts', with the numerous, different types of objects of non-interest (background), i.e., (non-target) components, present in the test solution or suspension (particularly those objects of non-interest (background), i.e., (non-target) components, which originated from the sample of matter).

Second, the background reducing chemical selectively, 'physicochemically interacts', during the hyper-spectral imaging, with the hyper-spectrally active target (i.e., the spectrally marked object of interest (target), i.e., spectrally marked (target) component) present in the test solution or suspension, in a manner which effectively (i.e., measurably) increases (enhances) its (spectral) luminescent (i.e., fluorescent or/and phosphorescent) properties, characteristics, and behavior. During the hyper-spectral imaging, the background reducing chemical may or may not effectively (i.e., measurably) 'chemically react', but at least to some extent 'physically interacts', with the hyper-spectrally active target (i.e., the spectrally marked object of interest (target), i.e., spectrally marked (target) component) present in the test solution or suspension.

Inclusion of the step (procedure) of adding to the test solution or suspension a background reducing chemical in the main step (procedure) of preparing a test solution or suspension of the sample of matter, results in achieving high levels of the important performance parameters of accuracy, precision (reproducibility), sensitivity, and resolution, at high speed (short time scale), be it during on-line (real time, near-real time) or off-line, in an optimum and highly efficient manner, of the remaining main steps (procedures) of the overall method, i.e., the main step (procedure) of generating and collecting hyper-spectral image data and information of the test solution or suspension, and the main step (procedure) of processing and analyzing the hyper-spectral image data and information, for identifying and characterizing the hyper-spectrally active target in the test solution or suspension, thereby identifying and characterizing the object of interest in the sample of matter.

Following completion of the preceding described main step (procedure) of preparing a test solution or suspension of the sample of matter, a portion or aliquot of the test solution or suspension of the sample of matter is then, preferably, transferred and placed on a clean, inert, metal slide or plate, or, on a clean, inert, plastic (e.g., Teflon®) or glass microscope type slide or plate, which is suitable for functioning as a sample holder in a hyper-spectral imaging and analysis system. The slide or plate (sample holder) with the portion or aliquot of the test solution or suspension of the sample of matter is then appropriately positioned and secured (fixed) upon a three-dimensionally movable (i.e., translational), and optionally, angularly movable (i.e., rotational), examination stage or platform of the hyper-spectral imaging and analysis system. Then, there is performing the next main step (procedure) of generating and collecting hyper-spectral image data and information of the test solution or suspension of the sample of matter.

>Exemplary Specific Embodiment for a Sample of Air (Air Sample) Containing Numerous Different Spatially or/and Temporally Varying Interfering Objects of Non-Interest (Background), and a Biological Agent or Chemical Agent Type of Object of Interest (Target)<

Performing the preceding main step (procedure) of preparing a test solution or suspension of the sample of matter is now described for an exemplary specific embodiment of the present invention, wherein the sample of matter is a sample of air (i.e., an air sample), and the object of interest is a biological agent (e.g., a bacterium [such as spore-forming bacterium *Bacillus anthracis*], a virus, a fungus, or a toxin), or a chemical agent (e.g., a nerve agent [e.g., sarin, tabun, or soman], or a chemical poison [e.g., a cyanide compound, or an organophosphate compound]). In general, the object of interest (i.e., biological agent or chemical agent) in the air sample is composed or made up of organic or/and inorganic materials or substances, which are in a solid (e.g., particulate) phase, a liquid (e.g., solution or suspension) phase, or/and a gaseous (e.g., aerosol) phase. Preferably, the object of interest (i.e., biological agent or chemical agent) in the air sample is composed or made up of organic or/and inorganic materials or substances, which are in a particulate form solid phase or/and are present (e.g., absorbed or/and adsorbed) on particles of the air sample. More specifically, for example, the object of interest can be a biological agent, such as the spore-forming bacterium *Bacillus anthracis*, which is chemically marked (e.g., via terbium trichloride [$TbCl_3$]), or biologically marked (e.g., via antibodies of an immunoassay technique), as part of the main step (procedure) of preparing a test solution or suspension of the sample of matter, i.e., the air sample, for enabling identification and characterization of the object of interest (i.e., the biological agent) via hyper-spectral imaging and analysis.

The sample of air is collected or obtained (e.g., via a standard type of air sampling or collecting system) from an indoor source of air (e.g., a post office, an airport, a subway station, a shopping mall, a sports arena, or an office building) or from an outdoor source of air. The air sample is typically collected or obtained on a (dry or pre-wetted) porous (filter-like or screen-like) solid substrate, such as a plastic or fiberglass (filter-like or screen-like) substrate, which functions like a filter, for filtering, capturing, and collecting a sample from the source of air.

The particulate matter of the air sample which is collected on the porous (filter-like or screen-like) solid substrate typically includes numerous, different types and concentrations of objects of non-interest, i.e., (non-target) components, such as dust, pollen, minerals, non-target types of biological matter (mold (fungi), bacteria), and non-target types of particulate chemical matter. Such (non-target) components of the air sample have relative concentrations which, typically, spatially vary or change (i.e., vary or change with position and location) or/and temporally vary or change (i.e., vary or change with time), depending upon the spatial or/and temporal variations in the local atmospheric environment and weather conditions of the indoor or outdoor source of air, and depending upon the location and time at which the air sample is collected or obtained from the air source. Therefore, a plurality of air samples is expected to have such spatially or/and temporally varying (non-target) components whose relative concentrations vary in accordance with their spatial or/and temporal variation in the source of air from which the air samples are collected or obtained.

The air sample which is collected on the porous (filter-like or screen-like) solid substrate may also include an object of interest (target), i.e., (target) component, such as a biological agent (e.g., a bacterium [such as spore-forming bacterium *Bacillus anthracis*], a virus, a fungus, or a toxin), or a chemical agent (e.g., a nerve agent [e.g., sarin, tabun, or soman], or a chemical poison [e.g., a cyanide compound, or an organophosphate compound]). Such a (target) component of the air sample has a relative concentration which, typically, spatially varies or changes (i.e., varies or changes with position and location) or/and temporally varies or changes (i.e., varies or changes with time), depending upon the spatial or/and temporal variations in the local atmospheric environment and weather conditions of the indoor or outdoor source of air, and depending upon the location and time at which the air sample is collected or obtained from the air source. Therefore, a plurality of air samples is expected to have such a spatially or/and temporally varying object of interest (target) whose relative concentration varies in accordance with its spatial or/and temporal variation in the source of air from which the air samples are collected or obtained.

Thus, following provision of the air sample, or following obtaining or collecting the air sample, there is preparing an appropriate test form of the air sample.

Utilizing the porous (filter-like or screen-like) solid substrate upon which is the collected particulate matter of the air sample, preferably, there is dissolving or suspending a relatively small quantity of the air sample into a solution or suspension form, for forming a test solution or suspension of the air sample. The procedure of dissolving, suspending, or/and mixing, i.e., reformulating, is performed using a liquid, for example, distilled water, or other liquid, which is suitable for dissolving or suspending the different types of objects of non-interest, i.e., (non-target) components present in the air sample (i.e., dust, pollen, minerals, non-target types of biological matter (mold (fungi), bacteria), and non-target types of particulate chemical matter), and which is suitable for dissolving or suspending the object of interest (target), such as a biological agent (e.g., a bacterium [such as spore-forming bacterium *Bacillus anthracis*], a virus, a fungus, or a toxin), or a chemical agent (e.g., nerve agent [e.g., sarin, tabun, or soman], or a chemical poison [e.g., a cyanide compound, or an organophosphate compound]).

The specific liquid used for dissolving, suspending, or/and mixing, i.e., reformulating, the small quantity of the air sample into a solution or suspension form, for forming a test solution or suspension test of the air sample, is selected whereby the liquid minimally affects hyper-spectral imaging and analysis of the numerous, different types of objects of non-interest, i.e., (non-target) components (i.e., dust, pollen, minerals, non-target types of biological matter (mold (fungi), bacteria), and non-target types of particulate chemical matter), present in the air sample (and subsequently present in the test solution or suspension), and whereby the liquid minimally affects hyper-spectral imaging and analysis of the object of interest (target), i.e., (target) component, such as a biological agent (e.g., a bacterium [such as spore-forming bacterium *Bacillus anthracis*], a virus, a fungus, or a toxin), or a chemical agent (e.g., a nerve agent [e.g., sarin, tabun, or soman], or a chemical poison [e.g., a cyanide compound, or an organophosphate compound]), present in the air sample (and subsequently present in the test solution or suspension).

Adding to the Air Sample a Spectral Marker Specific to the Biological Agent or Chemical Agent Often, the object of interest (target), such as a biological agent (e.g., a bacterium [such as spore-forming bacterium *Bacillus anthracis*], a virus, a fungus, or a toxin), or a chemical agent (e.g., a nerve agent [e.g., sarin, tabun, or soman], or a chemical poison [e.g., a cyanide compound, or an organophosphate compound]), by itself, is not 'spectrally' active, i.e., the biological agent or chemical agent (target) exhibits an insufficiently detectable or/and insufficiently measurable degree or extent of luminescent (i.e., fluorescent or/and phosphorescent) properties, characteristics, and behavior, when illuminated by electromagnetic radiation or light, such as ultra-violet (UV), visible (VIS), or infrared (IR), types of light.

Thus, the main step (procedure) of preparing a test solution or suspension of the air sample includes the step (procedure) of adding to the air sample, a spectral marker specific to the (target) biological agent or chemical agent, such that if the (target) biological agent or chemical agent is present in the test solution or suspension, the (target) biological agent or chemical agent when marked with the spectral marker becomes a hyper-spectrally active target which is hyper-spectrally detectable and identifiable in the test solution or suspension.

The spectral marker is, in general, a chemical type of spectral marker, or a biological type of spectral marker. A suitable chemical type of spectral marker is, in general, a chemical specie which interacts with (i.e., spectrally marks) the (target) biological agent or chemical agent for forming a {biological agent—chemical marker} complex or a {chemical agent—chemical marker} complex, respectively, which exhibits a detectable and measurable degree or extent of luminescent (i.e., fluorescent or/and phosphorescent) properties, characteristics, and behavior, when illuminated by different types of electromagnetic radiation or light, such as ultra-violet (UV), visible (VIS), or infrared (IR), types of light. A suitable biological type of spectral marker is, in general, a biological specie which interacts with (i.e., spectrally marks)

the (target) biological agent or chemical agent for forming a {biological agent—biological marker} complex or a {chemical agent—biological marker} complex, respectively, which exhibits some degree or extent of luminescent (i.e., fluorescent or/and phosphorescent) properties, characteristics, and behavior, when illuminated by different types of electromagnetic radiation or light, such as ultra-violet (UV), visible (VIS), or infrared (IR), types of light.

In any case of the (target) biological agent or chemical agent being spectrally marked with the chemical type of spectral marker, or with the biological type of spectral marker, the formed {biological agent—chemical marker} complex or {chemical agent—chemical marker} complex, respectively, or, the formed {biological agent—biological marker} complex or {chemical agent—biological marker} complex, respectively, becomes a hyper-spectrally active target which is hyper-spectrally detectable and identifiable in the test solution or suspension of the air sample, when the test solution or suspension is subjected to hyper-spectral imaging and analysis, thereby enabling identifying and characterizing the object of interest (i.e., biological agent or chemical agent) in the sample of matter.

Specific Case of the Biological Agent (e.g., Bacterium, Virus, Fungus, or Toxin) being the Spore-Forming Bacterium *Bacillus anthracis*

In a specific case of the exemplary specific embodiment of the present invention, wherein the sample of matter is a sample of air (i.e., an air sample), and the object of interest is a biological agent (e.g., bacterium, virus, fungus, or toxin), such as the spore-forming bacterium *Bacillus anthracis*, then, this main step (procedure) is performed as follows.

There is adding to the air sample, a spectral marker, specific to the (target) spore-forming bacterium *Bacillus anthracis*, such that if the (target) spore-forming bacterium *Bacillus anthracis* is present in the test solution or suspension, the (target) spore-forming bacterium *Bacillus anthracis* when marked with the spectral marker becomes a hyper-spectrally active target which is hyper-spectrally detectable and identifiable in the test solution or suspension.

In general, the spectral marker is added to the air sample immediately before or after, dissolving, suspending, or/and mixing, i.e., reformulating, the relatively small quantity of the air sample into a solution or suspension form.

The spectral marker is, in general, a chemical type of spectral marker, or a biological type of spectral marker. A suitable chemical type of spectral marker is a chemical specie, for example, terbium trichloride [$TbCl_3$], which interacts with (i.e., spectrally marks) the (target) spore-forming bacterium *Bacillus anthracis* (via dipicolinic acid [DPA] therein) for forming a {biological agent *Bacillus anthracis* spore (dipicolinic acid [DPA])—terbium trichloride [$TbCl_3$]} complex, which exhibits a detectable and measurable degree or extent of luminescent (i.e., fluorescent or/and phosphorescent) properties, characteristics, and behavior, when illuminated by different types of electromagnetic radiation or light, such as ultra-violet (UV), visible (VIS), or infrared (IR), types of light. A suitable biological type of spectral marker is a biological specie, for example, an antibody of an immunoassay technique (for example, as described in reference 37), which interacts with (i.e., spectrally marks) the (target) spore-forming bacterium *Bacillus anthracis* (via surface antigens thereof) for forming a {biological agent *Bacillus anthracis* spore antigen—antibody} complex, which exhibits a detectable and measurable degree or extent of luminescent (i.e., fluorescent or/and phosphorescent) properties, characteristics, and behavior, when illuminated by different types of electromagnetic radiation or light, such as ultra-violet (UV), visible (VIS), or infrared (IR), types of light.

In any case of the (target) spore-forming bacterium *Bacillus anthracis* being spectrally marked with the chemical type of spectral marker (i.e., terbium trichloride [$TbCl_3$]), or with the biological type of spectral marker (i.e., antibody), the formed {biological agent *Bacillus anthracis* spore (dipicolinic acid [DPA])—terbium trichloride [$TbCl_3$]} complex, or {biological agent *Bacillus anthracis* spore antigen—antibody} complex, respectively, becomes a hyper-spectrally active target which is hyper-spectrally detectable and identifiable in the test solution or suspension of the air sample, when the test solution or suspension is subjected to hyper-spectral imaging and analysis.

Specific Case of Adding to the Test Solution or Suspension a Background Reducing Chemical, for Example, an Organic Liquid, Such as Ethylene Glycol (MEG) [$HOCH_2CH_2OH$]

In accordance with the method of the present invention, as shown in FIG. 1, the main step (procedure) of preparing the test solution or suspension of the air sample includes the unique and critically important step (procedure) of adding to the test solution or suspension a background reducing chemical. The background reducing chemical reduces background interfering effects caused by presence of numerous, different types of objects of non-interest (background), i.e., (non-target) components, in the test solution or suspension (particularly those objects of non-interest (background), i.e., (non-target) components, which originated from the air sample), during the hyper-spectral imaging and analysis of the test solution or suspension, thereby increasing hyper-spectral detectability of the hyper-spectrally active target (i.e., the {biological agent *Bacillus anthracis* spore (dipicolinic acid [DPA])—terbium trichloride [$TbCl_3$]} complex, or the {biological agent *Bacillus anthracis* spore antigen—antibody} complex) in the test solution or suspension, and thus enhancing identification and characterization of the object of interest (i.e., the *Bacillus anthracis* biological agent) in the sample of matter.

The background reducing chemical is, in general, any type or kind of chemical which is composed or made up of one or more organic or/and inorganic materials or substances, which is/are in a solid (e.g., particulate) phase, a liquid (e.g., solution or suspension) phase, or a combination thereof.

In the specific case of the exemplary specific embodiment of the present invention, wherein the sample of matter is a sample of air (i.e., an air sample), and the object of interest is a biological agent (e.g., bacterium, virus, fungus, or toxin), such as the spore-forming bacterium *Bacillus anthracis*, it was empirically determined (see the Examples hereinbelow) that an exemplary preferred background reducing chemical is an organic liquid, such as ethylene glycol (i.e., monoethylene glycol (MEG) or ethane-1,2-diol) [$HOCH_2CH_2OH$].

The specific type or kind of background reducing chemical, i.e., the ethylene glycol (MEG) [$HOCH_2CH_2OH$], is selected such that the background reducing chemical effectively (i.e., measurably) reduces (decreases) background interfering effects caused by the presence of the numerous, different types of objects of non-interest (background), i.e., (non-target) components, in the test solution or suspension (particularly the numerous, spatially or/and temporally variable different types and concentrations of (non-target) components, such as dust, pollen, minerals, non-target types of biological matter (mold (fungi), bacteria), and non-target types of particulate chemical matter, which originated from the air sample), during the hyper-spectral imaging and analysis of the test solution or suspension. This results in increasing (enhancing) hyper-spectral detectability of the hyper-spectrally active target (i.e., the {biological agent *Bacillus anthracis* spore (dipicolinic acid [DPA])—terbium trichloride [$TbCl_3$]} complex, or the {biological agent to *Bacillus anthracis* spore antigen—antibody} complex) in the test solution or suspension, during the hyper-spectral imaging and analysis of the test solution or suspension. Accordingly, addition of the background reducing chemical, i.e., the ethylene glycol (MEG) [$HOCH_2CH_2OH$], to the test solution or suspension of the air sample results in increasing (enhancing) hyper-spectral detectability of the (target) spore-forming bacterium *Bacillus anthracis*, present in the air sample.

The background reducing chemical, i.e., the ethylene glycol (MEG) [$HOCH_2CH_2OH$], following addition to the test solution or suspension, and during the hyper-spectral imaging of the test solution or suspension, exhibits some combination of the following two main modes of behavior.

First, the background reducing chemical, i.e., the ethylene glycol (MEG) [$HOCH_2CH_2OH$], selectively, 'physicochemically interacts', during the hyper-spectral imaging, with a major portion of the numerous, different types of objects of non-interest (background), i.e., (non-target) components, present in the test solution or suspension (particularly those objects of non-interest (background), i.e., (non-target) components, which originated from the air sample), in a manner which effectively (i.e., measurably) reduces (decreases) their (spectral) luminescent (i.e., fluorescent or/and phosphorescent) properties, characteristics, and behavior. During the hyper-spectral imaging, the background reducing chemical, i.e., the ethylene glycol (MEG) [$HOCH_2CH_2OH$], may or may not effectively (i.e., measurably) 'chemically react', but at least to some extent 'physically interacts', with the numerous, different types of objects of non-interest (background), i.e., (non-target) components, present in the test solution or suspension (particularly including those objects of non-interest (background), i.e., (non-target) components, which originated from the air sample).

Second, the background reducing chemical, i.e., the ethylene glycol (MEG) [$HOCH_2CH_2OH$], selectively, 'physicochemically interacts', during the hyper-spectral imaging, with the hyper-spectrally active target (i.e., the {biological agent *Bacillus anthracis* spore (dipicolinic acid [DPA])—terbium trichloride [$TbCl_3$]} complex, or the {biological agent *Bacillus anthracis* spore antigen—antibody} complex) present in the test solution or suspension, in a manner which effectively (i.e., measurably) increases (enhances) its (spectral) luminescent (i.e., fluorescent or/and phosphorescent) properties, characteristics, and behavior. During the hyper-spectral imaging, the background reducing chemical, i.e., the ethylene glycol (MEG) [$HOCH_2CH_2OH$], may or may not effectively (i.e., measurably) 'chemically react', but at least to some extent 'physically interacts', with the hyper-spectrally active target (i.e., the {biological agent *Bacillus anthracis* spore (dipicolinic acid [DPA])—terbium trichloride [$TbCl_3$]} complex, or the {biological agent *Bacillus anthracis* spore antigen—antibody} complex) present in the test solution or suspension.

Inclusion of the step (procedure) of adding to the test solution or suspension a background reducing chemical, i.e., the ethylene glycol (MEG) [$HOCH_2CH_2OH$], in the main step (procedure) of preparing a test solution or suspension of the air sample, results in achieving high levels of the performance parameters of accuracy, precision (reproducibility), sensitivity, at high speed (short time scale), be it during on-line (real time, near-real time) or off-line, in an optimum and highly efficient manner, of the remaining main steps (procedures) of the method, i.e., the main step (procedure) of generating and collecting hyper-spectral image data and information of the test solution or suspension, and the main step (procedure) of processing and analyzing the hyper-spectral image data and information, for identifying and characterizing the hyper-spectrally active target (i.e., the {biological agent *Bacillus anthracis* spore (dipicolinic acid [DPA])—terbium trichloride [$TbCl_3$]} complex, or the {biological agent *Bacillus anthracis* spore antigen—antibody} complex) in the test solution or suspension, thereby identifying and characterizing the object of interest (i.e., the spore-forming bacterium *Bacillus anthracis*) in the air sample.

Following completion of the preceding described main step (procedure) of preparing a test solution or suspension of the air sample, a portion or aliquot of the test solution or suspension of the air sample is then, preferably, transferred and placed on a clean, inert, metal slide or plate, or, on a clean, inert, plastic (e.g., Teflon®) or glass microscope type slide or plate, which is suitable for functioning as a sample holder in a hyper-spectral imaging and analysis system. The slide or plate (sample holder) with the portion or aliquot of the test solution or suspension of the air sample is then appropriately positioned and secured (fixed) upon a three-dimensionally movable (i.e., translational), and optionally, angularly movable (i.e., rotational), examination stage or platform of the hyper-spectral imaging and analysis system. Then, there is performing the next main step (procedure) of generating and collecting hyper-spectral image data and information of the test solution or suspension of the air sample.

Generating and Collecting Hyper-Spectral Image Data and Information of the Test Solution or Suspension This main step (procedure) of the method for hyper-spectral imaging and analysis of a sample of matter, for identifying and characterizing an object of interest therein, of the present invention, is performed as described in the Field and Background section, hereinabove. In general, this main step (procedure) of generating and collecting hyper-spectral image data and information of the test solution or suspension of the sample of matter, is performed according to any suitable teaching or practice of generating and collecting hyper-spectral image data and information, using any suitable hyper-spectral imaging and analysis system and technique.

For example, for performing this main step (procedure) of the method of the present invention, there is using any suitable teaching or practice disclosed in references 1-29 (and references cited therein). Preferably, there is using the selected teachings and practices of hyper-spectral imaging and analysis by the same applicant/assignee of the present invention which are disclosed in references 30-36.

Accordingly, from the preceding described main step (procedure) of the method, the slide or plate (sample holder) with the portion or aliquot of the test solution or suspension of the sample of matter which is appropriately positioned and secured (fixed) upon a three-dimensionally movable (i.e., translational), and optionally, angularly movable (i.e., rotational), examination stage or platform of the hyper-spectral imaging and analysis system, is subjected to subjected to hyper-spectral imaging and analysis. Multiple fields of view of the sample of matter are 'hyper-spectrally' scanned and imaged while the sample of matter (containing objects, and components thereof) is exposed to electromagnetic radiation. During the hyper-spectral scanning and imaging there is generating and collecting relatively large numbers (up to the order of millions) of multiple spectral (i.e., hyper-spectral) images, 'one-at-a-time', but, in an extremely fast or rapid sequential manner, of the objects (and components thereof) emitting electromagnetic radiation at a plurality of many wavelengths and frequencies, where the wavelengths and frequencies are associated with different selected (relatively narrow) portions or bands, or bands therein, of an entire hyper-spectrum emitted by the objects (and components thereof) of the sample of matter.

The hyper-spectral imaging and analysis system can be operated in an extremely fast or rapid manner for providing exceptionally highly resolved spectral and spatial data and information of the imaged sample of matter (containing the objects, and components thereof).

>Exemplary Specific Embodiment for a Sample of Air (Air Sample) Containing Numerous Different Spatially or/and Temporally Varying Interfering Objects of Non-Interest (Background), and a Biological Agent or Chemical Agent Type of Object of Interest (Target)<

This main step (procedure) is readily performed for generating and collecting hyper-spectral image data and information of the test solution or suspension, for the exemplary specific embodiment of the present invention, wherein the sample of matter is a sample of air (i.e., an air sample), and the object of interest is a biological agent (e.g., a bacterium, a virus, a fungus, or a toxin), or a chemical agent (e.g., a nerve agent [e.g., sarin, tabun, or soman], or a chemical poison [e.g., a cyanide compound, or an organophosphate compound]), which is composed or made up of organic or/and inorganic materials or substances that are preferably in a solid (e.g., particulate) phase or/and are present (e.g., absorbed or/and adsorbed) on particles of the air sample. More specifically, for example, the object of interest can be a biological agent, such as the spore-forming bacterium *Bacillus anthracis*, which is chemically marked (e.g., via terbium trichloride [$TbCl_3$]), or biologically marked (e.g., via antibodies of an immunoassay technique), as described hereinabove, as part of the main step (procedure) of preparing a test solution or suspension of the sample of matter, i.e., the air sample, for enabling identification and characterization of the objects of interest (i.e., the biological agent spore-forming bacterium *Bacillus anthracis*) via hyper-spectral imaging and analysis.

In some embodiments of the present invention, the main step (procedure) of generating and collecting hyper-spectral image data and information of the test solution or suspension includes 'separately' generating and collecting (acquiring) hyper-spectral image data and information of objects of non-interest.

Accordingly, there is 'separately' acquiring hyper-spectral image data and information of background interfering effects caused by the presence of the numerous, different types of objects of non-interest (background), i.e., (non-target) components, present in the test solution or suspension (particularly the numerous, spatially or/and temporally variable different types and concentrations of (non-target) components, such as dust, pollen, minerals, non-target types of biological matter (mold (fungi), bacteria), and non-target types of particulate chemical matter, which originated from the air sample), during the hyper-spectral imaging and analysis of the test solution or suspension.

In exemplary embodiments, there is acquiring the hyper-spectral image data and information for different types and concentrations of any one or more of the objects of non-interest (background) in a 'dry form' (for example, as exemplified herein below in Examples 1 and 2), or additionally, or alternatively, in a 'wet form' dissolved or suspended in a liquid (for example, as exemplified herein below in Example 2). For example, according to a 'wet form', there is dissolving or suspending exemplary objects of non-interest, such as dust or pollen particles in the same background reducing chemical, e.g., ethylene glycol (MEG) [$HOCH_2CH_2OH$], which is used in the main step (procedure) of preparing a test solution or suspension of the sample of matter.

Processing and Analyzing the Hyper-Spectral Image Data and Information

This main step (procedure) of the method for hyper-spectral imaging and analysis of a sample of matter, for identifying and characterizing an object of interest therein, of the present invention, is performed as described in the Field and Background section, hereinabove. In general, this main step (procedure) of processing and analyzing the hyper-spectral image data and information, for identifying and characterizing the hyper-spectrally active target in the test solution or suspension, thereby identifying and characterizing the object of interest in the sample of matter, is performed according to any suitable prior art teaching or practice of processing and analyzing hyper-spectral image data and information, for identifying and characterizing a hyper-spectrally active target in a test solution or suspension, using any suitable hyper-spectral imaging and analysis system taught about or practiced in the prior art.

For example, for performing this main step (procedure) of the method of the present invention, there is using any suitable teaching or practice disclosed in references 1-29 (and references cited therein). Preferably, there is using the selected teachings and practices of hyper-spectral imaging and analysis by the same applicant/assignee of the present invention which are disclosed in references 30-36.

Accordingly, the hyper-spectral images generated by, and collected from, the sample of matter, are correlated with emission spectra of the sample of matter, where the emission spectra correspond to spectral representations in the form of spectral 'fingerprint' or 'signature' pattern types of identification and characterization, of the hyper-spectrally imaged objects (and components thereof) in the sample of matter. Such hyper-spectral image data and information are processed and analyzed by using automatic pattern recognition (APR) or/and optical character recognition (OCR) types of hyper-spectral imaging data and information processing and analysis, for identifying, characterizing, or/and classifying, the physical, chemical, or/and biological, properties, characteristics, and behavior, of the hyper-spectrally imaged objects (and components thereof) in the sample of matter.

According to some embodiments of the method for hyper-spectral imaging and analysis of a sample of matter, for identifying and characterizing an object of interest therein, processing and analyzing the hyper-spectral image data and information includes the following sub-steps (sub-procedures), which are considered additional special technical features of exemplary embodiments of the disclosed invention:

- evaluating a detectability level of the hyper-spectrally active target in the test solution or suspension according to three criteria: (1) area of all positive pixels in a hyper-spectral image expressing characteristic spectral finger prints of light emitted by the hyper-spectrally active target, (2) fluorescence intensity of every positive pixel in the hyper-spectral image that expresses the characteristic spectral finger prints of the hyper-spectrally active target, and (3) relationship between the characteristic spectral finger prints included in the positive pixels of the hyper-spectral image and of a hyper-spectral image database.
- analyzing the hyper-spectral image for the characteristic spectral finger prints at a one pixel resolution, and calculating total area that subtends all the positive pixels for each hyper-spectral image and concentration of the spectral marker.
- calculating minimum, maximum, and average intensities of a spectral region around a characteristic emission peak of the hyper-spectrally active target.

creating two distinct data bases, wherein a first data base corresponds to all available spectra of the background interfering effects, and a second data base includes all spectra corresponding to the hyper-spectrally active target.

comparing spectral finger prints incorporated in the positive pixels of the hyper-spectral image to spectral finger prints from the two distinct data bases, whereby the positive pixels are divided into the hyper-spectrally active target and the background interfering effects, and then correlating, for yielding percentage of the positive pixels corresponding to the hyper-spectrally active target and percentage of the positive pixels corresponding to the background interfering effects.

using (plotting) the percentages of positive pixels in a bar graph for showing distribution of the characteristic spectral finger prints of the hyper-spectrally active target and of the background interfering effects among the positive pixels of the hyper-spectrally active target, as a function of a count of the object of interest.

>Exemplary Specific Embodiment for a Sample of Air (Air Sample) Containing Numerous Different Spatially or/and Temporally Varying Interfering Objects of Non-Interest (Background), and a Biological Agent or Chemical Agent Type of Object of Interest (Target)<

This main step (procedure) is readily performed for processing and analyzing the hyper-spectral image data and information, for identifying and characterizing the hyper-spectrally active target in the test solution or suspension, thereby identifying and characterizing the object of interest in the sample of matter, for the exemplary specific preferred embodiment of the present invention, wherein the sample of matter is a sample of air (i.e., an air sample), and the object of interest is a biological agent (e.g., a bacterium, a virus, a fungus, or a toxin), or a chemical agent (e.g., a nerve agent [e.g., sarin, tabun, or soman], or a chemical poison [e.g., a cyanide compound, or an organophosphate compound]). More specifically, for example, the object of interest can be a biological agent, such as the spore-forming bacterium *Bacillus anthracis*, which is chemically marked (e.g., via terbium trichloride [$TbCl_3$]), or biologically marked (e.g., via antibodies of an immunoassay technique), as described hereinabove, as part of the main step (procedure) of preparing a test solution or suspension of the sample of matter, i.e., the air sample, for enabling identification and characterization of the objects of interest (i.e., the biological agent spore-forming bacterium *Bacillus anthracis*) via hyper-spectral imaging and analysis.

In some embodiments of the present invention, the main step (procedure) of processing and analyzing the hyper-spectral image data and information, includes processing and analyzing hyper-spectral image data and information of objects of non-interest. For example, this main step (procedure) includes processing and analyzing the hyper-spectral image data and information that is 'separately' generated and collected (acquired) via the preceding main step (procedure) of generating and collecting hyper-spectral image data and information of the test solution or suspension of the sample of matter.

Accordingly, the hyper-spectral images generated by, and collected from, the objects of non-interest are correlated with emission spectra of the sample of matter, where the emission spectra correspond to spectral representations in the form of spectral 'fingerprint' or 'signature' pattern types of identification and characterization, of the hyper-spectrally imaged objects (and components thereof) of non-interest which are present in the sample of matter. Such hyper-spectral image data and information are processed and analyzed by using automatic pattern recognition (APR) or/and optical character recognition (OCR) types of hyper-spectral imaging data and information processing and analysis, for identifying, characterizing, or/and classifying, the physical, chemical, or/and biological, properties, characteristics, and behavior, of the hyper-spectrally imaged objects (and components thereof) of non-interest present in the sample of matter. This additional step (procedure) of processing and analyzing hyper-spectral image data and information of objects of non-interest provides useful data and information used for identifying and characterizing hyper-spectrally active targets of non-interest in the test solution or suspension, which assist in identifying and characterizing the object of interest in the sample of matter.

EXAMPLES

Selected embodiments of the present invention, including novel and inventive aspects, characteristics, special technical features, and advantages thereof, as illustratively described hereinabove, and as claimed in the claims section hereinbelow, are exemplified and have experimental support in the following examples, which are not intended to be limiting.

Materials and Procedures

Hyper-Spectral Imaging and Analysis System

In each of the Examples 1-3, the same hyper-spectral imaging and analysis system was used: the Green Vision Systems Ltd. (Tel Aviv, Israel) manufactured hyper-spectral imaging (optical scanning) and analysis system, model names: HyperEye® Detection System, FIPA® (Fluorescence Imaging Particle Analyzer), and FIPA-20® (Fluorescence Imaging Particle Analyzer), including the following main components and operational features or conditions.

Sample illuminating (light beam) source: mercury lamp, 100 W (watts), with a narrow band pass filter centered at 334 or 365 nanometers (nm) and bandwidth of ±10 nm.

Optical scan bandwidth: at or within the range of 400-900 nm

Digital analysis range: 400-900 nm.

Optics: objective, ×10 Zeiss Ultrafluar®, with a pixel size of 6.45 microns (μ)×6.45μ.

Wavelength resolution: 1.5 nm.

The hyper-spectral imaging and analysis system included a three-dimensionally movable (i.e., translational), and angularly movable (i.e., rotational), examination stage or platform, upon which were placed test samples.

Chemical and Biological Reagents

Water (Examples 1-3, for washing and rinsing): distilled deionized filtered water, generated by a research laboratory grade water purification system, was exclusively used throughout.

Ethanol (Examples 2, 3): dehydrated ethyl alcohol, ≥85.0%, Sigma-Aldrich (no. 636-1).

Ethylene glycol (Examples 2 and 3): ethylene glycol (monoethylene glycol (MEG) or ethane-1,2-diol) [$HOCH_2CH_2OH$], ≥98.0%, Sigma-Aldrich (Fluka brand, no. 03760).

Dipicolinic acid [DPA] (Example 3): 2,6-pyridinedicarboxylic acid, 99%, Sigma-Aldrich (Aldrich brand, no. P63808).

Terbium trichloride [$TbCl_3$] (Example 3): terbium (III) chloride, anhydrous powder, 99% (metal basis), Sigma-Aldrich (Aldrich brand, no. 439657).

Biological agent, *Bacillus subtilis* spores (Examples 3 and 4): *Bacillus subtilis* (ATCC 6633), lyophilized cells, Sigma-Aldrich (Sigma brand, no. B4006). The (non-hazardous) biological agent *Bacillus subtilis* was used as a functional equivalent substitute for the (extremely hazardous) biological agent *Bacillus anthracis*.

General Experimental Methods and Procedures

Examples 1-3 are 'actual' or 'working' examples, wherein the described and illustrated experimental methodologies and procedures were developed and performed, and the experimental results were obtained, by the same applicant/assignee of the present invention.

In Example 3, preparing test solutions or suspensions of the indicated samples of matter were performed according to the hereinabove description of the present invention.

In Examples 1-3, generating and collecting, and, processing and analyzing, the hyper-spectral image data and information of the indicated samples of matter were performed according to the hereinabove description of the present invention, according to the selected teachings and practices of hyper-spectral imaging and analysis by the same applicant/assignee of the present invention which are disclosed in references 30-36.

Example 4 is 'prophetic', wherein the (prophetic) experimental methodology and procedures were developed by the same applicant/assignee of the present invention.

Example 1

Hyper-Spectral Imaging and Analysis of 'Dust Particles' Present in a Sample of Air Collected from an Indoor Source of Air In Example 1, (dry form) dust particles of different sizes and shapes present in samples of air (i.e., air samples) collected from an indoor source of air (absent of any particular object of interest (target), such as a biological agent or chemical agent) were subjected to hyper-spectral imaging and analysis. The main objective was for obtaining hyper-spectral image data and information in the form of images and spectral fingerprint (SFP) or spectral signature pattern types of identification and characterization of the various different sized and shaped dust particles present in the source of air, for serving as a useful reference associated with 'objects of non-interest' (background) during hyper-spectrally imaging and analyzing of similarly collected air samples, or of other types of samples of matter, which may have present an 'object of interest' (target), such as a biological agent or chemical agent.

Experimental Methods and Procedures

Samples of air (air samples) were collected, using a standard type of air sampling or collecting system, from an indoor source of air (absent of any particular object of interest (target), such as a biological agent or chemical agent), being air in the immediate vicinity where postal workers handle and process letters inside a post office. The post office normally had closed windows, with a standard type of HVAC (heating, ventilation, air conditioning) environmental control. Each air sample was collected on a (dry or pre-wetted) porous plastic or fiberglass (filter-like or screen-like) substrate, which functioned like a filter, for filtering, capturing, and collecting, a sample from the source of air.

The indoor source of air typically included numerous, spatially or/and temporally variable different types and concentrations of components, such as dust (fine, dry particles of matter), pollen (fine particulate or powderlike material consisting of pollen grains produced by plants), minerals, non-target types of biological matter (mold (fungi), bacteria), and non-target types of particulate chemical matter. All such components present in the collected air samples were composed or made up of organic or/and inorganic materials or substances, which were in a particulate form solid phase or/and were present (e.g., absorbed or/and adsorbed) on particles of the collected air samples, and were collectively classified and treated as 'dust particles'. The dust particles had a characteristic size in the range of between about 1 micron and about 20 microns, and were of different shapes.

For each air sample, a portion of the (dry form) dust particles was placed (spread out) on a clean, inert, glass microscope type slide or plate which functioned as a sample holder in the hyper-spectral imaging and analysis system. The slide or plate (sample holder) with the portion of the dust particles was then appropriately positioned and secured (fixed) upon the examination stage or platform of the hyper-spectral imaging and analysis system. Fifty separate (individual) dust particles, of different sizes and shapes, were hyper-spectrally scanned and imaged, for obtaining hyper-spectral images and spectral fingerprint (SFP) or spectral signature pattern types of identification and characterization.

Results

The results for two exemplary and representative separate (individual) dust particles of the fifty separate (individual) dust particles which were subjected to the hyper-spectral imaging and analysis are presented in FIGS. 2a and 2b, which are exemplary empirically determined graphical plots (spectra) of Emission Intensity (normalized) as a function of Emission Wavelength (nm) of exemplary dust particles 1 and 2, respectively, showing the spectral fingerprints (SFPs) thereof. FIGS. 2a and 2b show that each of dust particle 1 and dust particle 2, respectively, is characterized by essentially the same spectral fingerprint (SFP) having essentially the same characteristic shape, and same characteristic emission intensity maximum or peak at an emission wavelength of about 460 nm.

Example 2

Hyper-Spectral Imaging and Analysis of (Native) 'Dust Particles' Suspended in Different Liquids (Ethanol, or Ethylene Glycol), for Determining Extent of 'Background' Signal Reduction Effected by Each Liquid In Example 2, (native) dust particles of different sizes and shapes manually collected from dust originating from an indoor source of air (absent of any particular object of interest (target), such as a biological agent or chemical agent) were suspended in different liquids (ethanol, or ethylene glycol) and subjected to hyper-spectral imaging and analysis. The main objective was for obtaining hyper-spectral image data and information in the form of hyper-spectral images and spectral fingerprint (SFP) or spectral signature pattern types of identification and characterization of the suspended dust particles (as exemplary test suspensions), for determining the extent or degree of background signal reduction that could be effected by each suspending liquid. The experimental data and information serves as useful reference associated with 'objects of non-interest' (background) during hyper-spectrally imaging and analyzing of air samples, or of other types of samples of matter, which may have present an 'object of interest' (target), such as a biological agent or chemical agent.

Experimental Methods and Procedures (Native) dust particles were manually collected (using inert 'dust free' surgical type clean gloves and a metal spatula) from a normally clean, 'dusty' desktop. The dust particles originated from an indoor source of air (absent of any particular object of interest, such as a biological agent or chemical agent), being air of a business office which normally had closed windows, with a standard type of HVAC (heating, ventilation, air conditioning) environmental control.

As for Example 1, the indoor source of air typically included numerous, spatially or/and temporally variable different types and concentrations of components, such as dust, pollen, minerals, non-target types of biological matter, and non-target types of particulate chemical matter. All such components present in the collected dust samples were composed or made up of organic or/and inorganic materials or substances, which were in a particulate form solid phase or/and were present (e.g., absorbed or/and adsorbed) on particles of the indoor air, and were collectively classified and treated as 'dust particles'. The dust particles had a characteristic size in the range of between about 1 micron and about 20 microns, and were of different shapes.

A series of three types of samples (sample types) were prepared and tested: (Type 1 samples): dry form dust particles (as a baseline reference or control) absent of any liquid; (Type 2 samples): a test suspension of dust particles suspended in ethanol; and (Type 3 samples): a test suspension of dust particles suspended in ethylene glycol.

For each sample type (1, 2, and 3), a portion or aliquot of each sample was placed on a clean, inert, glass microscope type slide or plate which functioned as a sample holder in the hyper-spectral imaging and analysis system. The slide or plate (sample holder) with the sample portion or aliquot was then appropriately positioned and secured (fixed) upon the examination stage or platform of the hyper-spectral imaging and analysis system. For each sample type, several separate (individual) dust particles, of different sizes and shapes, were hyper-spectrally scanned and imaged, for obtaining hyper-spectral images and spectral fingerprint (SFP) or spectral signature pattern types of identification and characterization.

Results

At an exemplary characteristic emission wavelength of about 460 nm, the 'average' emission intensity (in terms of absolute arbitrary units) for each of the three sample types tested was as follows:

Type 1 samples: dry form dust particles (baseline reference or control): 12,700.

Type 2 samples: test suspension of dust particles suspended in ethanol: 11,700.

Type 3 samples: test suspension of dust particles suspended in ethylene glycol: 1,600.

Relative to dry form dust particles (as a baseline reference or control), the results show that the ethanol had a relatively very minor effect (i.e., a decrease of only 1000 units) on reducing the background signal (average emission intensity) primarily due to the dust particles in Type 2 samples. By strong contrast, the ethylene glycol had a relatively very major effect (i.e., a decrease of 11,100 units) on reducing the background signal (average emission intensity) primarily due to the dust particles in Type 3 samples. Based on the results, it was concluded that for the experimental samples and conditions used and tested in Example 2, ethylene glycol is capable of significantly reducing background signal (average emission intensity) due to dust particles which are present in a test suspension of a sample of matter. It was therefore concluded that ethylene glycol is a 'viable' and effective background reducing chemical for use in hyper-spectral imaging and analysis of a sample of matter.

Example 3

Hyper-Spectral Imaging and Analysis of Target-Containing Test Suspensions of [(Dipicolinic Acid [DPA])—Terbium Trichloride [TbCl$_3$]] Complex, and of Target-Containing Test Suspensions of {Biological Agent *Bacillus subtilis* Spore (Dipicolinic Acid [DPA])—Terbium Trichloride [TbCl$_3$]} Complex], Suspended in the Background Reducing Chemical being Ethylene Glycol The rapid and accurate identification of biological agents is a vital task for first-responders in order to facilitate timely and appropriate actions in the event of a biological attack. *Bacillus anthracis*, a spore-forming bacterium and a dangerous pathogen causing the anthrax disease, is an important example. Among the potential biological warfare agent candidates, *Bacillus anthracis* spores are of particular concern. First, they are highly resistant to environmental stress and are relatively easily produced into weapon-grade material outside the laboratory. Second, anthrax is an infectious disease, requiring medical attention within 24-48 hours of initial inhalation of more than 104 *Bacillus anthracis* spores. However, the diagnosis of anthrax is not immediate since it takes 1-60 days for anthrax symptoms to appear in humans. Therefore, the rapid detection of *Bacillus anthracis* spores in the environment prior to infection is an extremely important goal for human safety.

*Bacillus anthracis* bacteria may exist in a spore form. Structurally, a spore consists of a central core surrounded by various protective layers. Dipicolinic acid [DPA] is found in these protective layers and accounts for about 10% of the spore's dry weight. The dipicolinic acid [DPA] can be exploited by being complexed to a chemical type of spectral marker, for example, terbium trichloride [TbCl$_3$], which interacts with (i.e., spectrally marks) the spore-forming bacterium *Bacillus anthracis* (via the dipicolinic acid [DPA] therein) for forming a {biological agent *Bacillus anthracis* spore (dipicolinic acid [DPA])—terbium trichloride [TbCl$_3$]} complex. The formed complex exhibits a detectable and measurable degree or extent of luminescent (i.e., fluorescent or/and phosphorescent) properties, characteristics, and behavior, when illuminated by different types of electromagnetic radiation or light, such as ultra-violet (UV), visible (VIS), or infrared (IR), types of light.

In Example 3, the (non-hazardous) biological agent *Bacillus subtilis* was used as a functional equivalent substitute for the (extremely hazardous) biological agent *Bacillus anthracis*. A main objective of Example 3 was to implement the present invention with respect to: (i) the detectability of the {(dipicolinic acid [DPA])—terbium trichloride [TbCl$_3$]} complexes, (ii) the detectability of {biological agent *Bacillus subtilis* spore (dipicolinic acid [DPA])—terbium trichloride [TbCl$_3$]} complexes, and (iii) the detectability of {biological agent *Bacillus subtilis* spore (dipicolinic acid [DPA])—terbium trichloride [TbCl$_3$]} complexes with the background of native dust particles, and (iv) data base creation, identification, and decision making.

Experimental Methods and Procedures

During all measurements the experiments room was completely darkened.

The detectability level was evaluated by three distinct criteria: (1) the area of all pixels expressing the characteristic spectral finger print (SFP) of light emitted whether a {(dipicolinic acid [DPA])—terbium trichloride [TbCl$_3$]} complex was exited by a UV light (herein, referred to as Positive Pixels), (2) the fluorescence intensity of every pixel that expresses the characteristic SFP of {(dipicolinic acid [DPA])—terbium trichloride [TbCl$_3$]} complexes, and (3) the relationship between SFPs included in Positive Pixels of a given image and spectral database.

(i) Detectability of {(Dipicolinic Acid [DPA])—Terbium Trichloride [TbCl$_3$]} Complexes In order to examine the level of detection of {[DPA]—[TbCl$_3$]} complexes by the hyper-spectral imaging and analysis system, 10 μl (microliters) of DPA and [TbCl$_3$] solutions (prepared in ethanol) were applied on a black metal plate, and three spectral images were acquired for each DPA concentration.

Reagents

[TbCl$_3$]: 8 mM (millimolar).

DPA: 30 mM, 15 mM, 500 μM (micromolar), 50 μM, 5 μM, 500 nM (nanomolar), 50 nM, and 5 nM.

As a control, 10 μl of [TbCl$_3$], 25 mM applied on a black metal plate was assayed.

Data Analysis

Hyper-spectral images were analyzed for the characteristic spectrum emitted by the {[DPA]—[TbCl$_3$]} complexes at a one pixel resolution, and the total area subtends all positive pixels was calculated for each hyper-spectral image and DPA concentration. Moreover, the minimum, maximum, and average intensities of the spectral region around the characteristic emission peak of the {[DPA]—[TbCl$_3$]} complex (540±5 nm) were calculated.

Results

The level of detection of {[DPA]—[TbCl$_3$]} complexes was found to increase with DPA concentration. Generally, the percentage of pixels (out of all pixels contained in each of the acquired spectral images) expressing the characteristic spectral finger print (SFP) of {[DPA]—[TbCl$_3$]} complexes (positive pixels) increased with increasing DPA concentration. The highest percentage of positive pixels was found at a DPA concentration of 30 mM, while the lowest percentage was achieved at the lowest examined DPA concentration, 5 nM. Additionally, when only [TbCl$_3$] was assayed, only 7.2% of the pixels were shown to be positive. The average intensity of the emission peak of the {[DPA]—[TbCl$_3$]} complex decreased with DPA concentration until achieving a steady-state around a DPA concentration of 50 μM.

(ii) Detectability of {Biological Agent *Bacillus subtilis* Spore (Dipicolinic Acid [DPA])—Terbium Trichloride [TbCl$_3$]} Complexes The (non-hazardous) biological agent *Bacillus subtilis* was used as a functional equivalent substitute for the (extremely hazardous) biological agent *Bacillus anthracis*.

In order to examine the level of detection of {biological agent *Bacillus subtilis* spore (dipicolinic acid [DPA])—terbium trichloride [TbCl$_3$]} complexes, spore suspensions of different concentrations were prepared. Given a stock suspension of *Bacillus subtilis* spores, five consecutive dilutions were performed. Prior to examining the detectability, spores of the highest dilution were counted using a standard hemocytometer. The number of spores in each of the dilutions was calculated by multiplying the number of spores in the highest dilution by the ratio between the highest dilution and the dilution in concern. In order to release the DPA molecules from within the spores, the later were broken down by heating at 80° C. for 15 minutes. The heat treated spores were stored at a 4° C. until the spore detectability was examined.

The experimental procedure included the application of 10 μl of preheated spore suspension, 10 μl of [TbCl$_3$] 40 μM solution, and 15 μl of ethylene glycol (background reducing chemical) on a white Teflon® plate. The following final concentrations were achieved: 7.2×10$^6$, 7.2×10$^5$, 7.2×10$^4$, 7.2× 10$^3$, and 7.2×10$^2$ spores/ml (milliliter). Samples were examined using the hyper-spectral imaging and analysis system.

Results

The level of detection of complexes comprising of DPA (extracted from *Bacillus subtilis* spores) and [TbCl$_3$] molecules was examined. The vast majority of pixels contained in the acquired spectral images expressed the characteristic spectral finger print (SFP) of {[DPA]—[TbCl$_3$]} complexes (positive pixels). Throughout the various spore concentrations, the fluorescence intensity of all positive pixels was found to decrease with spore concentration. The highest fluorescence intensity resulted out of the illumination of a sample including 7.2×10$^6$ while the lowest fluorescence intensity was achieved when a sample comprising of 7.2×10$^2$ spores/ml was illuminated. The results are presented in FIGS. 3a and 3b.

FIG. 3a is an exemplary empirically determined graphical plot (spectrum) of Emission Intensity (normalized) as a function of Emission Wavelength (nm) of a background-only test suspension [containing only objects of non-interest suspended in the exemplary background reducing chemical being the organic liquid ethylene glycol (monoethylene glycol (MEG)); absent of any object of interest or target (i.e., absent of a hyper-spectrally active target being the exemplary {biological agent *Bacillus subtilis* spore (dipicolinic acid [DPA])—terbium trichloride [TbCl$_3$]} complex], subjected to hyper-spectral imaging and analysis, showing the spectral fingerprint (SFP) thereof.

FIG. 3b is an exemplary empirically determined graphical plot (spectrum) of Emission Intensity (normalized) as a function of Emission Wavelength (nm) of a target-containing test suspension [including objects of non-interest, and an exemplary object of interest or target (i.e., a hyper-spectrally active target being the exemplary {biological agent *Bacillus subtilis* spore (dipicolinic acid [DPA])—terbium trichloride [TbCl$_3$]} complex, suspended in the exemplary background reducing chemical being the organic liquid ethylene glycol (monoethylene glycol (MEG))], subjected to hyper-spectral imaging and analysis, showing the spectral fingerprints (SFPs) thereof. In FIG. 3b, the following reference numbers, in terms of the SFPs are applicable to the indicated concentrations:

SFP 5: 7.2×10$^2$ spores/ml.
SFP 4: 7.2×10$^3$ spores/ml.
SFP 2, 3: 7.2×10$^4$ spores/ml, 7.2×10$^5$, spores/ml.
SFP 1: 7.2×10$^6$ spores/ml.

(iii) Detectability of {Biological Agent *Bacillus subtilis* Spore (Dipicolinic Acid [DPA])—Terbium Trichloride [TbCl$_3$]} Complexes on (Native) Dust Background To test the detectability of {biological agent *Bacillus subtilis* spore (dipicolinic acid [DPA])—terbium trichloride [TbCl$_3$]} complexes on the background of (native) dust, three different spore suspensions were assayed using the hyper-spectral imaging and analysis system. Since the total number of particles to be positioned on the sample plate is 15 millions, the number of particles to be spread on the chemical section of the sample plate is 3.75 millions. Dust particles ranging between 1 and 20 μm in dimension, were suspended in distilled water and using a hemocytometer, spores were counted. 3.75 million dust particles (200 μl (microliters) of dust particles suspension) were applied and evenly spread on a white Teflon® plate. 10 μl of spore suspension (preheated to achieve the disruption of the spores and the extraction of DPA molecules) were added to the sample plate. The dust-spore suspension was partly evaporated by heating the sample with an IR light source, and 10 μl of [TbCl$_3$] 40 mM (final concentration equals 6 mM) and 50 μl of ethylene glycol (as background reducing chemical) was added.

The detectability of the {biological agent *Bacillus subtilis* spore (dipicolinic acid [DPA])—terbium trichloride [$TbCl_3$]} complexes on the background of native dust was evaluated at 6 different spore suspensions containing: 2,500; 5,000; 25,000; 50,000; 250,000 and 2,500,000 spores. Apart from these spore suspensions, a sample containing all reagents but the spores was assayed as a control. Five hyper-spectral images were acquired at each spore suspension. That is, conforming to the detectability requirements of 9000 spores/15,000,000 particles.

Results

The detectability level of complexes comprising of DPA (extracted from *Bacillus subtilis* spores) and [$TbCl_3$] molecules on a dusty background was examined using the hyper-spectral imaging and analysis system. The percentage of positive pixels (pixels expressing the characteristic spectral finger print (SFP) of the {biological agent *Bacillus subtilis* spore (dipicolinic acid [DPA])—terbium trichloride [$TbCl_3$]} complexes) contained in the acquired hyper-spectral images increased with growing spore count. That is, 12% of the pixels subtending the hyper-spectral images of the highest spore count ($2.5 \times 10^6$ spores) were found to be positive. On the other hand, only 1.35% of the pixels included in hyper-spectral images taken at a spore count of $2.5 \times 10^3$ were positive. The percentage of Positive Pixels in the images of the control sample (without spores) was found to be 3.16%. Therefore, the last spore suspension to result in a Positive Pixel percentage higher than that of the control sample is the one yielded from the suspension of $2.5 \times 10^4$ spores. The hyper-spectral imaging and analysis system was capable of detecting spore suspensions containing at least 25,000 spores.

(iv) Data Base Creation, Identification, and Decision Making

Apart from analyzing the hyper-spectral images for the exact emission peak of the {biological agent *Bacillus subtilis* spore (dipicolinic acid [DPA])—terbium trichloride [$TbCl_3$]} complex, another approach under taken was to create large data bases comprising all hyper-spectra included in the acquired hyper-spectral images. Following the identification of the emission peak of interest, all pixels not expressing the exact emission peak (negative pixels) were discarded from further analyses. Spectral finger prints (SFPs) included within the Positive Pixels were compared against the hyper-spectral data bases as a second stage validation and a decision was made.

Creating the Background and Target Databases

Two distinct data bases were created. The first corresponds to all available spectra of the dusty and particulate background ('background'), and the other included all spectra corresponding to the *Bacillus subtilis* spores ('target'). Following the identification of the emission peak, spectral finger prints (SFPs) included within the Positive Pixels were detected, analyzed, grouped, and placed into the 'target' data base. The 'target' data base included all the SFPs detected in 30 spectral images acquired at six different spore counts. The 'background' data base was generated by taking into account all SFPs included in the Positive Pixels found in 5 spectral images of dusty background.

Decision Stage

By comparing the SFPs incorporated in the Positive Pixels of a given image to SFPs from the 'target' and 'background' data bases, Positive Pixels were divided into 'target' and background then correlated. This division yielded the percentage of Positive Pixels corresponding to 'target' and the percentage of those matching to 'background'. The decision to be made is based on this pixel distribution, and by so, takes into account the presence of the exact emission peak of the {biological agent *Bacillus subtilis* spore (dipicolinic acid [DPA])—terbium trichloride [$TbCl_3$]} complex together with the relationships between the newly acquired SFPs and a large spectral data base.

Results

Results of the above described data base creation, identification, and decision making are presented in FIGS. 4a and 4b.

FIG. 4a is an exemplary empirically determined bar graph of Positive Pixels (%) as a function of Spore Count (absolute number) showing distribution of 'background' and 'target' spectral fingerprints (SFPs) among Positive Pixels [of the emission peak (540±5 nm) of an exemplary object of interest or target (i.e., a hyper-spectrally active target being the exemplary {biological agent *Bacillus subtilis* spore (dipicolinic acid [DPA])—terbium trichloride [$TbCl_3$]} complex], as a function of Spore Count, based on hyper-spectral image data and information obtained from FIGS. 3a and 3b and similar experiments.

FIG. 4b is an exemplary empirically determined bar graph of Positive Pixels (%) as a function of Spore Count (absolute number) showing 'reproducibility' of the distribution of 'background' and 'target' spectral fingerprints (SFPs) among Positive Pixels [of the emission peak (540±5 nm) of an exemplary object of interest or target (i.e., a hyper-spectrally active target being the exemplary {biological agent *Bacillus subtilis* spore (dipicolinic acid [DPA])—terbium trichloride [$TbCl_3$]} complex], as a function of Spore Count, based on hyper-spectral image data and information obtained by repeating experiments of Example 3, as described hereinbelow in Example 4, in accordance with the present invention.

For generating the results presented in FIG. 4b, the detectability of the {biological agent *Bacillus subtilis* spore (dipicolinic acid [DPA])—terbium trichloride [$TbCl_3$]} complexes on the background of native dust was evaluated at 5 different spore suspensions containing: 4,500; 9,000; 45,000; 90,000; and 450,000 spores. Apart from these spore suspensions, a sample containing all reagents but the spores was assayed as a control. Five hyper-spectral images were acquired at each spore suspension. That is, conforming to the detectability requirements of 9000 spores/15,000,000 particles.

Example 4 (Prophetic)

Hyper-Spectral Imaging and Analysis of Target-Containing Test Solutions or Suspensions of (Biological Agent *Bacillus subtilis* Spore Antigen—Antibody} Complex], Including the Background Reducing Chemical being Ethylene Glycol

*Bacillus subtilis* Spores Detection by Immunofluorescence Microscopy—Hyper-Spectral Imaging and Analysis Sample Preparation

*Bacillus subtilis* spore suspensions (105-106/ml) are fixed in 0.1% glutaraldehyde in PBS for 10 min Samples (10 µl) are immediately applied to microscope coverslips (BDH) that are treated with 0.01% (wt/vol) poly-L-lysine (Sigma) (see below).

After 4 min, the liquid is aspirated from the slide, which is then allowed to dry completely in air at room temperature.

The coverslip is washed in phosphate-buffered saline (PBS) (pH 7.4) and if needed blocked for 15 min with 2% bovine serum albumin (BSA) (Sigma BSA) in PBS at room temperature, and then washed again.

Samples are incubated with 50 µl of staining solution (see below) for 5, 10, or 15 minutes.

The samples are rinsed with 10 ml of PBS using gentle flow from a 10 ml pipette.

An aliquot of ethylene glycol is added to the sample as a background reducing chemical.

The coverslips are mounted onto a microscope slide, followed by performing hyper-spectral imaging and analysis of the samples as described hereinabove.

Polylysine-Coated Coverslips (Polylysine-Coated Microscope Slides, (Sigma))

Sonicate the coverslips (12 mm) in acetone for 15 min at room temperature.

Wash the coverslips with distilled water (dH2O) to remove completely the acetone.

Place the coverslips on a clean paper sheet separing each others. Leave the coverslips dry at air.

Gently spread 20 ml polylysine (Sigma) solution (0.1 mg/ml dH2O) on the coverslips surface.

Leave the polylysine drops on the coverslips dry at room temperature.

Staining Solution:

A 1:1 mix of primary and secondary antibodies in PBS+1% BSA:

Antibody dilutions from 1 mg/ml stock solution: 1:100/1:500/1:2500/1:12500.

Primary Antibody:

Rabbit purified polyclonal anti *Bacillus subtilis/Bacillus cereus* spores (USBiological catalog #B0003-27).

Secondary Antibody:

Goat anti rabbit IgG (H+L) ML. The following four options are possible, depending on microscope properties: Cy conjugates are better than FITC or TRITC (slower photobleaching). (Jackson Immunoresearch Laboratories).

Cy2 conjugate (A=492/E=510 nm) Cat #111-225-144 (Green fluorescence).

FITC conjugate (A=492/E=520 nm) Cat #111-095-144 (Green fluorescence).

TRITC conjugate (A=550/E=570 nm) Cat #111-025-144 (Red fluorescence).

Cy3 conjugate (A=550/E=570 nm) Cat #111-165-144 (Red fluorescence).

The present invention, as illustratively described and exemplified hereinabove, has several beneficial and advantageous aspects, characteristics, and features.

First, the present invention is generally applicable for on-line (e.g., real time or near-real time) or off-line hyper-spectral imaging and analysis of various different types or kinds of samples of matter, wherein the matter, and at least one object of interest therein, are composed or made up of organic or/and inorganic materials or substances, which are in a solid (e.g., particulate) phase, a liquid (e.g., solution or suspension) phase, or/and a gaseous (e.g., aerosol) phase. The present invention provides the capability of achieving the 'ultimate' combination of the highly desirable performance parameters of high accuracy, 'and' high precision (high reproducibility), 'and' high sensitivity, 'and' high resolution, 'and' at high speed (short time scale), all at the same time (i.e., simultaneously), be it during on-line or off-line, in an optimum and highly efficient manner.

Second, the present invention is particularly implementable in applications involving on-line (real time or near-real time) or off-line hyper-spectral imaging and analysis of a sample of air (i.e., an air sample), for identifying and characterizing an object of interest therein, wherein the object of interest is a biological agent (e.g., a bacterium, a virus, a fungus, or a toxin), or a chemical agent (e.g., a nerve agent [e.g., sarin, tabun, or soman], or a chemical poison [e.g., a cyanide compound, or an organophosphate compound]).

Third, the present invention is particularly implementable in applications where the sample of air is collected or obtained (e.g., via a standard type of air sampling or collecting system) from an indoor source of air (e.g., a post office, an airport, a subway station, a shopping mall, a sports arena, or an office building), or from an outdoor source of air.

Fourth, the present invention is particularly implementable in applications wherein the object of interest is a biological agent or a chemical agent. More specifically, wherein the sample of matter is a sample of air (i.e., an air sample), and the object of interest is a biological agent (e.g., a bacterium, a virus, a fungus, or a toxin), or a chemical agent (e.g., a nerve agent [e.g., sarin, tabun, or soman], or a chemical poison [e.g., a cyanide compound, or a organophosphate compound]). In general, the object of interest (i.e., biological agent or chemical agent) in the air sample is composed or made up of organic or/and inorganic materials or substances, which are in a solid (e.g., particulate) phase, a liquid (e.g., solution or suspension) phase, or/and a gaseous (e.g., aerosol) phase. Preferably, the object of interest (i.e., biological agent or chemical agent) in the air sample is composed or made up of organic or/and inorganic materials or substances, which are in a particulate form solid phase or/and are present (e.g., absorbed or/and adsorbed) on particles of the air sample.

The object of interest can be a biological agent, such as the spore-forming bacterium *Bacillus anthracis*, which is chemically marked (e.g., via terbium trichloride [$TbCl_3$]), or biologically marked (e.g., via antibodies of an immunoassay technique), as part of the main step (procedure) of preparing a test solution or suspension of the sample of matter, i.e., the air sample, for enabling identification and characterization thereof via hyper-spectral imaging and analysis.

Fifth, the present invention is particularly implementable in essentially any field or area of science and technology involving an application which is based on, or involves, the need for on-line (real time or near-real time) or off-line analyzing a sample of matter, for a main purpose or objective of identifying and characterizing at least one object (i.e., entity, material, substance) of interest, usually among a variety of different types or kinds of objects (i.e., entities, materials, substances) of non-interest, in the sample of matter. Such characterization may include determining any number and types or kinds of biological, chemical, or/and physical, properties, characteristics, features, parameters, or/and behavior, of the at least one object of interest in the sample of matter.

Based on the preceding, the present invention successfully addresses and overcomes various significant shortcomings and limitations, and widens the scope, of presently known techniques and methods of hyper-spectral imaging and analysis of a sample of matter. In particular, the present invention successfully addresses and overcomes the significantly problematic and complicating aspects, and corresponding negative affects and influences, due to the spatially or/and temporally varying presence of objects of non-interest (background) in a sample of matter, such as a sample of air.

The present invention is readily commercially applicable to a wide variety of different industries.

It is to be fully understood that certain aspects, characteristics, and features, of the invention, which are illustratively described and presented in the context or format of a plurality of separate embodiments, may also be illustratively described and presented in any suitable combination or sub-combination in the context or format of a single embodiment. Conversely, various aspects, characteristics, and features, of the invention, which are illustratively described and presented in combination or sub-combination in the context or format of a single embodiment, may also be illustratively described and presented in the context or format of a plurality of separate embodiments.

Although the invention has been illustratively described and presented by way of preferred and specific embodiments, and examples thereof, it is evident that many alternatives, modifications, and variations, thereof, will be apparent to those skilled in the art. Accordingly, it is intended that all such alternatives, modifications, and variations, fall within, and are encompassed by, the scope of the appended claims.

All references (patents, patent applications, and publications) cited or referred to in this specification are herein incorporated in their entirety by reference into the specification, to the same extent as if each individual reference (patent, patent application, or publication) was specifically and individually indicated to be incorporated herein by reference. In addition, citation or identification of any reference in this specification shall not be construed or understood as an admission that such reference represents or corresponds to prior art of the present invention.

REFERENCES

1. U.S. Pat. Appl. No. 20070002159, to Olsen, et al., entitled: "Method And Apparatus For Use In Camera And Systems Employing Same".
2. U.S. Pat. Appl. No. 20060092414, to Geshwind, et al., entitled: "Devices And Method For Spectral Measurements".
3. U.S. Pat. Appl. No. 20060074835, to Maggioni, et al., entitled: "System And Method For Hyper-spectral Analysis".
4. U.S. Pat. Appl. No. 20050270528, to Geshwind, et al., entitled: "Hyper-spectral Imaging Methods And Devices".
5. U.S. Pat. Appl. No. 20050254709, to Geshwind, et al., entitled: "System And Method For Hyper-spectral Analysis".
6. U.S. Pat. Appl. No. 20050213089, to Margalith, et al., entitled: "Spectral Imaging Device With Tunable Light Source".
7. U.S. Pat. No. 7,148,967, to Slagle, entitled: "Hyper-spectral/continuously-tunable Imager".
8 (a,b). U.S. Pat. Nos. 7,080,912 (a), and 6,886,953 (b), each to Cook, entitled: "High-resolution, All-reflective Imaging Spectrometer".
9. U.S. Pat. No. 7,074,622, to Qiao, et al., entitled: "Method And System For Sorting And Separating Particles".
10. U.S. Pat. No. 7,046,859, to Bernstein, et al., entitled: "Methods For Determining A Measure Of Atmospheric Aerosol Optical Properties Using A Multi- or Hyperspectral, Multi-pixel Image".
11 (a,b). U.S. Pat. Nos. 6,999,165 (a), and 6,995,840 (b), each to Hagler, entitled: "Method And Apparatus For Radiation Encoding And Analysis".
12. U.S. Pat. No. 6,992,809, to Wang, et al., entitled: "Multi-conjugate Liquid Crystal Tunable Filter".
13 (a,b,c). U.S. Pat. Nos. 6,922,645 (a), 6,842,702 (b), and 6,687,620 (c), each to Haaland, et al., each entitled: "Augmented Classical Least Squares Multivariate Spectral Analysis".
14. U.S. Pat. No. 6,912,322, to Smith, et al., entitled: "Adaptive Process For Removing Streaks In Multi-band Digital Images".
15. U.S. Pat. No. 6,859,275, to Fateley, et al., entitled: "System And Method For Encoded Spatio-spectral Information Processing".
16. U.S. Pat. No. 6,724,940, to Qian, et al., entitled: "System And Method For Encoding Multidimensional Data Using Hierarchical Self-organizing Cluster Vector Quantization".
17 (a,b). U.S. Pat. Nos. 6,711,503 (a), and 6,341,257 (b), each to Haaland, each entitled: "Hybrid Least Squares Multivariate Spectral Analysis Methods".
18. U.S. Pat. No. 6,701,021, to Qian, et al., entitled: "System And Method For Encoding/Decoding Multidimensional Data Using Successive Approximation Multi-stage Vector Quantization".
19. U.S. Pat. No. 6,546,146, to Hollinger, et al., entitled: "System For Interactive Visualization And Analysis Of Imaging Spectrometry Datasets Over A Wide-area Network".
20. U.S. Pat. No. 6,415,233, to Haaland, entitled: "Classical Least Squares Multivariate Spectral Analysis".
21. U.S. Pat. No. 6,018,587, to Cabib, entitled: "Method For Remote Sensing Analysis By Decorrelation Statistical Analysis And Hardware Therefor".
22. U.S. Pat. No. 5,782,770, to Mooradian, et al., entitled: "Hyperspectral Imaging Methods And Apparatus For Non-invasive Diagnosis Of Tissue For Cancer".
23. U.S. Pat. No. 5,724,135, to Bernhardt, entitled: "Hyperspectral Imaging Using Rotational Spectro-tomography".
24. *Fluorescence Imaging Spectroscopy and Microscopy*, edited by Wang, X. F., and Herman, B., Vol. 137 of *Chemical Analysis*, edited by Winefordner, J. D., published by John Wiley & Sons, Inc., New York (1996).
25. *Computer-Assisted Microscopy—The Measurement and Analysis of Images*, by Russ, J. C., published by Plenum Press, New York, Plenum Publishing Corp., New York, USA (1990).
26. *Fourier Transforms in Spectroscopy*, by Kauppinen, J., and Partanen, J., 1st edition, published by Wiley-VCH Verlag Berlin GmbH, Berlin, Germany (2001).
27. *Fundamentals of Fourier Transform Infrared Spectroscopy*, by Smith, B. C., published by CRC Press LLC, Florida, USA (1996).
28. "Classification Of Multispectral Image Data By Extraction And Classification Of Homogeneous Objects", Kettig, R. L. and Landgrebe, D., *IEEE Transactions on Geoscience Electronics*, Vol. GE14, 19 (1976).
29. "Pattern Classification And Recognition Based On Morphology And Neural Networks", Yu, P., Anastassopoulos, V., and Venetsanopoulos, A. N., *Can. J. Elect. and Comp. Eng.*, Vol. 17, No. 2, 58-59 (1992).
30. WIPO PCT Pat. Appl. Int'l. Pub. No. WO 2007/0990540, published Sep. 7, 2007, of PCT Pat. Appl. No. IL2007/000268, filed Mar. 1, 2007, of same applicant/assignee as the present invention, entitled: "Processing And Analyzing Hyper-spectral Image Data And Information Via Dynamic Database Updating".
31. WIPO PCT Pat. Appl. Intl Pub. No. WO 2003/085371, published Oct. 16, 2003, of PCT Pat. Appl. No. IL03/00292, filed Apr. 7, 2003, of same applicant/assignee as the present invention, entitled: "Real Time High Speed High Resolution Hyper-spectral Imaging".
32. U.S. Pat. No. 6,697,510, to Moshe, of same applicant/assignee as the present invention, entitled: "Method For Generating Intra-particle Crystallographic Parameter Maps And Histograms Of A Chemically Pure Crystalline Particulate Substance".
33. U.S. Pat. No. 6,694,048, to Moshe, of same applicant/assignee as the present invention, entitled: "Method For Generating Intra-particle Morphological Concentration/Density Maps And Histograms Of A Chemically Pure Particulate Substance".

34. U.S. Pat. No. 6,438,261, to Moshe, et al., of same applicant/assignee as the present invention, entitled: "Method Of In-situ Focus-fusion Multi-layer Spectral Imaging And Analysis".

35. U.S. Pat. No. 6,091,843, to Horesh, et al., of same applicant/assignee as the present invention, entitled: "Method Of Calibration And Real-time Analysis Of Particulates".

36. U.S. Pat. No. 5,880,830, to Schechter, of same applicant/assignee as the present invention, entitled: "Spectral Imaging Method For On-line Analysis Of Polycyclic Aromatic Hydrocarbons In Aerosols".

37. "Monoclonal Antibodies for *Bacillus anthracis* Spore Detection and Functional Analyses of Spore Germination and Outgrowth", Swiecki, M. K.; Lisanby, M. W.; Shu, F.; Turnbough, C. L., Jr.; and Kearney, J. F., *J. Immunol.*, Vol. 176, No. 10, 6076-84 (May 15, 2006).

What is claimed is:

1. A method for hyper-spectral imaging and analysis of a sample of matter, for identifying and characterizing an object of interest therein, the method comprising:

preparing a test solution or suspension of the sample of matter, said preparing includes adding to the sample of matter a spectral marker specific to the object of interest, such that if the object of interest is present in said test solution or suspension, the object of interest when marked with said spectral marker becomes a hyper-spectrally active target which is hyper-spectrally detectable and identifiable in said test solution or suspension;

generating and collecting hyper-spectral image data and information of said test solution or suspension; and processing and analyzing said hyper-spectral image data and information, for identifying and characterizing said hyper-spectrally active target in said test solution or suspension, thereby identifying and characterizing the object of interest in the sample of matter;

wherein said preparing said test solution or suspension includes adding to said test solution or suspension a background reducing chemical, wherein said background reducing chemical reduces background interfering effects caused by presence of objects of non-interest in said test solution or suspension, during the hyper-spectral imaging and analysis, thereby increasing hyper-spectral detectability of said hyper-spectrally active target in said test solution or suspension; and wherein said generating and collecting said hyper-spectral image data and information of said test solution or suspension includes separately acquiring hyper-spectral image data and information of said objects of non-interest.

2. The method of claim 1, wherein the sample of matter is a sample of air.

3. The method of claim 1, wherein the object of interest is a biological agent or a chemical agent.

4. The method of claim 3, wherein said biological agent is selected from the group consisting of a bacterium, a virus, a fungus, and a toxin.

5. The method of claim 1, wherein said spectral marker specific to the object of interest is selected from the group consisting of chemical markers and biological markers.

6. The method of claim 5, wherein said chemical marker is terbium trichloride [$TbCl_3$].

7. The method of claim 5, wherein said biological marker is an antibody of an immunoassay technique.

8. The method of claim 1, wherein said background reducing chemical is selected from the group consisting of solids, and liquids.

9. The method of claim 8, wherein said liquid is an organic liquid.

10. The method of claim 9, wherein said organic liquid is ethylene glycol (monoethylene glycol (MEG) or ethane-1,2-diol) [$HOCH_2CH_2OH$].

11. The method of claim 1, wherein said separately acquiring said hyper-spectral image data and information of said objects of non-interest is performed for one or more of said objects of non-interest selected from the group consisting of dust, pollen, minerals, non-target types of biological matter, and non-target types of particulate chemical matter.

12. The method of claim 1, wherein said separately acquiring said hyper-spectral image data and information of said objects of non-interest is performed for one or more of said objects of non-interest in a dry form.

13. The method of claim 1, wherein said separately acquiring said hyper-spectral image data and information of said objects of non-interest is performed for one or more of said objects of non-interest in a wet form dissolved or suspended in said background reducing chemical.

14. The method of claim 13, wherein said background reducing chemical is ethylene glycol.

15. The method of claim 1, wherein said processing and analyzing said hyper-spectral image data and information includes evaluating a detectability level of said hyper-spectrally active target in said test solution or suspension according to three criteria: (1) area of all positive pixels in a hyper-spectral image expressing characteristic spectral finger prints of light emitted by said hyper-spectrally active target, (2) fluorescence intensity of every said positive pixel in said hyper-spectral image that expresses said characteristic spectral finger prints of said hyper-spectrally active target, and (3) relationship between said characteristic spectral finger prints included in said positive pixels of said hyper-spectral image and of a hyper-spectral image database.

16. The method of claim 15, further including analyzing said hyper-spectral image for said characteristic spectral finger prints at a one pixel resolution, and calculating total said area that subtends all said positive pixels for each said hyper-spectral image and concentration of said spectral marker.

17. The method of claim 15, further including calculating minimum, maximum, and average intensities of a spectral region around a characteristic emission peak of said hyper-spectrally active target.

18. The method of claim 15, further including creating two distinct data bases, wherein a first data base corresponds to all available spectra of said background interfering effects, and a second data base includes all spectra corresponding to said hyper-spectrally active target.

19. The method of claim 18, further including comparing spectral finger prints incorporated in said positive pixels of said hyper-spectral image to spectral finger prints from said two distinct data bases, whereby said positive pixels are divided into said hyper-spectrally active target and said background interfering effects, and then correlating, for yielding percentage of said positive pixels corresponding to said hyper-spectrally active target and percentage of said positive pixels corresponding to said background interfering effects.

20. The method of claim 19, wherein said percentages of positive pixels are used in a bar graph for showing distribution of said characteristic spectral finger prints of said hyper-spectrally active target and of said background interfering effects among said positive pixels of said hyper-spectrally active target, as a function of a count of the object of interest.

* * * * *